(12) United States Patent
Allier et al.

(10) Patent No.: US 12,339,215 B2
(45) Date of Patent: Jun. 24, 2025

(54) METHOD FOR DETERMINING THE VIABILITY OF CELLS

(71) Applicants: COMMISSARIAT À L'ENERGIE ATOMIQUE ET AUX ENERGIES ALTERNATIVES, Paris (FR); IPRASENSE SAS, Clapiers (FR); GLAXOSMITHKLINE INTELLECTUAL PROPERTY DEVELOPMENT LIMITED, Brentford (GB)

(72) Inventors: Cedric Allier, Grenoble (FR); Lionel Herve, Grenoble (FR); Geoffrey Esteban, Teyran (FR); Martin Pisaneschi, Jacou (FR); Melissa Hill, King of Prussia, PA (US)

(73) Assignees: COMMISSARIAT A L'ENERGIE ATOMIQUE ET AUX ENERGIES ALTERNATIVES, Paris (FR); IPRASENSE SAS, Clapiers (FR); GLAXOSMITHKLINE INTELLECTUAL PROPERTY DEVELOPMENT LIMITED, Stevenage (GB)

( * ) Notice: Subject to any disclaimer, the term of this patent is extended or adjusted under 35 U.S.C. 154(b) by 438 days.

(21) Appl. No.: 17/995,775

(22) PCT Filed: Apr. 8, 2020

(86) PCT No.: PCT/US2020/027263
§ 371 (c)(1),
(2) Date: Oct. 7, 2022

(87) PCT Pub. No.: WO2021/206707
PCT Pub. Date: Oct. 14, 2021

(65) Prior Publication Data
US 2023/0168180 A1 Jun. 1, 2023

(51) Int. Cl.
*G01N 15/1433* (2024.01)
*C12M 1/34* (2006.01)
*G01N 15/14* (2006.01)

(52) U.S. Cl.
CPC ......... *G01N 15/1433* (2024.01); *C12M 41/46* (2013.01); *G01N 2015/1488* (2013.01); *G01N 2510/00* (2013.01)

(58) Field of Classification Search
CPC ....... G01N 15/1433; G01N 2015/1488; G01N 2510/00; G01N 2015/1006; C12M 41/46
See application file for complete search history.

(56) References Cited

U.S. PATENT DOCUMENTS

| 4,735,504 A | 4/1988 | Tycko |
| 7,948,632 B2 | 5/2011 | Gustafsson et al. |

(Continued)

OTHER PUBLICATIONS

Curl, C. et al., ("Refractive index measurement in viable cells using quantitative phase-amplitude microscopy and confocal microscopy," Cytometry Part A, vol. 65A, 2005, pp. 88-92) (Year: 2005, USA) (Year: 2005).*

(Continued)

*Primary Examiner* — Amara Abdi
(74) *Attorney, Agent, or Firm* — Oblon, McClelland, Maier & Neustadt, L.L.P.

(57) ABSTRACT

A method for determining a state of a cell, the cell being placed in a sample in contact with a culture medium, includes illuminating the sample with a light source and acquiring an image of the sample with an image sensor, the image sensor lying in a detection plane. From the acquired image, a position of the cell in a plane parallel to the detection plane is located and a refractive index or a relative refractive index of the cell is estimated, the relative refractive index corresponding to a refractive index of the cell relative to the refractive index of the culture medium. From (Continued)

the estimation, an index of interest of the cell is determined. From the index, a state of the cell among predetermined states is classified, the predetermined states including at least one apoptosis state and one living state.

19 Claims, 13 Drawing Sheets

(56) References Cited

U.S. PATENT DOCUMENTS

| | | | | |
|---|---|---|---|---|
| 8,260,063 | B2* | 9/2012 | Hasezawa | G06F 18/2115 |
| | | | | 382/225 |
| 2004/0052730 | A1* | 3/2004 | Hochman | G01N 33/5005 |
| | | | | 424/9.2 |
| 2010/0093015 | A1 | 4/2010 | Panza et al. | |
| 2010/0254589 | A1* | 10/2010 | Gallagher | G06V 20/695 |
| | | | | 382/133 |
| 2013/0210066 | A1* | 8/2013 | Pavillon | G03H 1/0866 |
| | | | | 435/288.7 |
| 2014/0291524 | A1* | 10/2014 | Kubota | G01N 21/3586 |
| | | | | 250/341.8 |
| 2018/0067111 | A1 | 3/2018 | Segal et al. | |
| 2018/0113064 | A1* | 4/2018 | Allier | G01N 15/1433 |
| 2019/0101482 | A1* | 4/2019 | Allier | G01N 15/1429 |

OTHER PUBLICATIONS

Curl, C. et al., "Refractive index measurement in viable cells using quantitative phase-amplitude microscopy and confocal microscopy," Cytometry Part A, vol. 65A, 2005, pp. 88-92, XP093131814.
Extended European Search Report issued Mar. 15, 2024 in European Patent Application No. 20930474.0, 10 pages.
International Search Report issued Jul. 17, 2020 in PCT/US2020/027263 filed on Apr. 8, 2020, 3 pages.

* cited by examiner

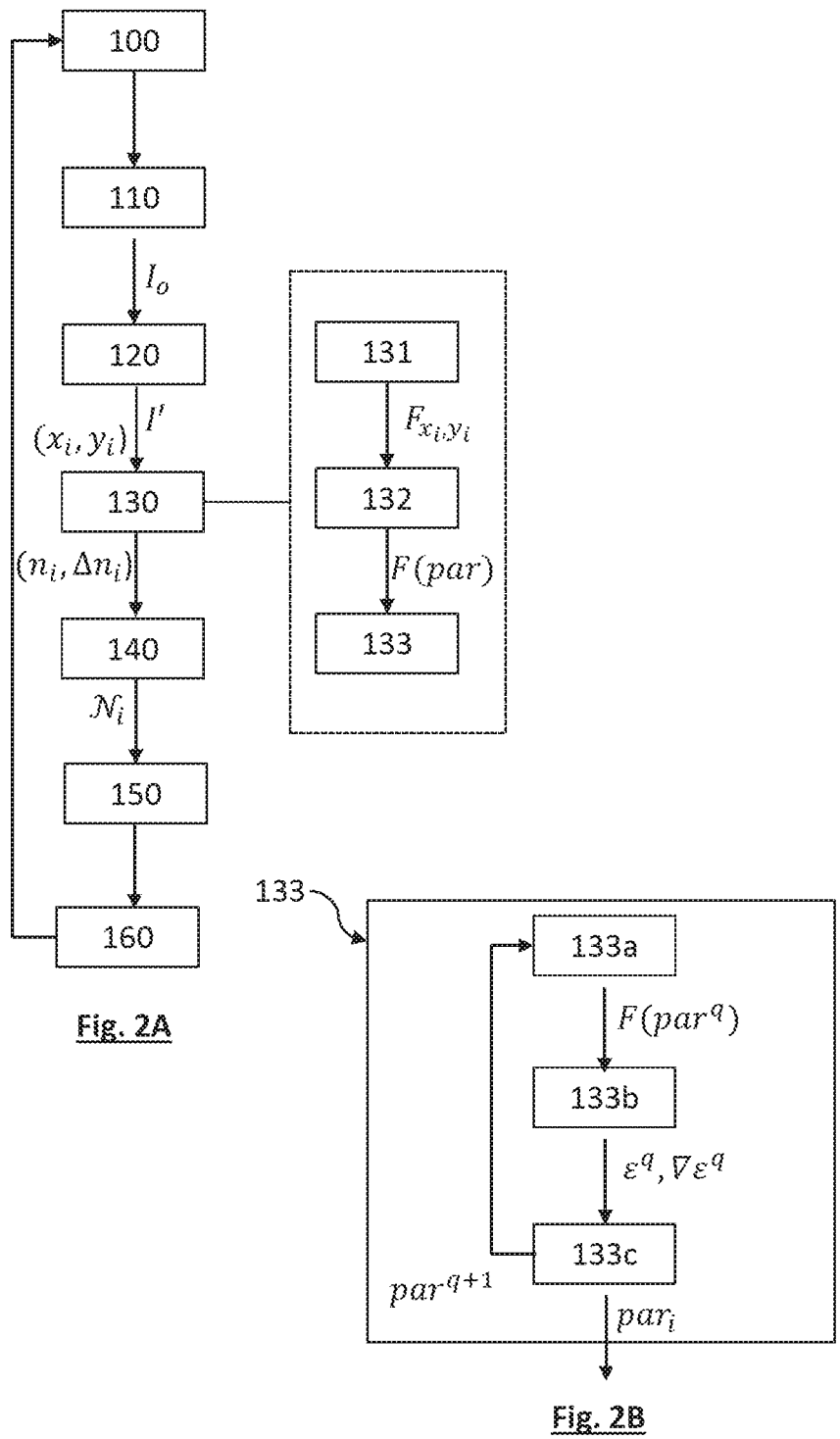

| 0.045 | 0.035 | 0.025 | 0.015 | 0.05 |

METHOD FOR DETERMINING THE VIABILITY OF CELLS

TECHNICAL FIELD

The technical field of the invention is the analysis of images of cells in order to determine a state of said cells. It is in particular a question of determining a living or dead cellular state, including the occurrence of apoptosis.

PRIOR ART

Cells are cultured in bioreactors in many pharmaceutical or medical fields, in order to produce molecules for therapeutic purposes. Which may, for example, be proteins, vaccines or antibodies. However, cells are fragile. The composition of the biological medium, and hydrodynamic stresses (stirring of the medium) to which the cells are subjected may limit the viability of the cells. When the viability of the cells decreases, i.e. when the number of dead cells increase, the yield of the production decreases. It is therefore important to detect, or even to limit as much as possible, the death of cells cultivated in bioreactors.

There are two types of cellular death, which may occur in vivo but also in vitro: necrosis and apoptosis. Necrosis occurs accidentally, and rapidly, following a malfunction of a cell, in particular, following a perturbation of the culture medium. Apoptosis is a programmed cellular death by self-destruction, the process of which may take several hours. In a bioreactor, apoptosis is also considered to be influenced by the culture physicochemical conditions, for example a lack of oxygen, a lack of nutrients, or the accumulation of toxic metabolites. The hydrodynamic conditions in the bioreactor may also lead to apoptosis, notably when the culture medium is stirred too vigorously. It will be understood that the optimization of culture conditions is essential to improving the yield of production in a bioreactor.

Currently, on the industrial scale, the main optical devices for estimating cellular viability are based on the use of viability markers, based on color (marking with trypan blue) or fluorescence (marking with propidium iodide). An optical method not using marking has been described in U.S. Pat. No. 10,481,076.

One objective of the invention is to provide a device and method for analyzing cellular viability without marking, allowing simultaneous characterization of the state of viability of a high number of cells. One notable advantage of the method is that it allows an occurrence of apoptosis to be detected or even prevented.

DESCRIPTION OF THE INVENTION

An object of the invention is a method for determining a state of a cell, the cell being placed in a sample, in contact with a culture medium, the method comprising:
a) illuminating the sample with a light source and acquiring an image of the sample with an image sensor, the image sensor lying in a detection plane;
b) from the acquired image, locating a position of the cell in a plane parallel to the detection plane;
the method further comprising:
c) from the acquired image, estimating a refractive index of the cell or a relative refractive index of the cell, the relative refractive index corresponding to a refractive index of the cell relative to the refractive index of the culture medium;
d) from the estimation of the refractive index or of the relative refractive index, determining an index of interest of the cell;
e) from the index of interest, classifying a state of the cell among predetermined states, the predetermined states comprising at least one apoptosis state and one living state.

In one embodiment,
in c), the refractive index or the relative refractive index is a complex quantity;
in d), the index of interest comprises a real part of the refractive index or of the relative refractive index.

In one embodiment,
in c), the refractive index or the relative refractive index is a complex quantity;
in d), the index of interest is determined depending on a real part and/or on an imaginary part of the refractive index or of the relative refractive index.

The index of interest may be determined from a difference or from a weighted difference between the real part and the imaginary part of the refractive index or of the relative refractive index.

By from the acquired image, what is meant is using the acquired image so as to locate the position of the cell. This may comprise reconstructing a complex image of an exposure light wave, propagating between the sample and the image sensor.

In one embodiment, step e) comprises:
taking into account a threshold;
comparing the index of interest with the threshold.

In one embodiment, step e) comprises taking into account a reference range, the reference range comprising index of interest corresponding to living cells. The apoptosis state corresponds to an index of interest outside of the reference range. The predetermined states may comprise at least one dead state. The dead state and the apoptosis state may correspond to an index of interest lying respectively on one side and on another side of the reference range.

In one embodiment,
steps b) to d) are carried out for a plurality of cells, each cell of the plurality of cells being considered as a living cell, so as to obtain a distribution of the index of interest of said cells;
in step e), the reference range is defined from the distribution.

The method may comprise determining the threshold based on the distribution of the index of interest.

The method may comprise determining a reference value from the distribution. The state of each cell may be determined depending on a deviation between the reference value and the index of interest of said cell.

In one embodiment,
a) is carried out at various times, so as to obtain an image of the sample each time;
b) to e) are carried out successively using the images obtained at each time;
in each step e), the predetermined states comprise at least one dead cellular state;
the method comprises a step f) of computing a viability at each time, the viability depending on a number of cells considered to be living, dead and in apoptosis, respectively.

In one embodiment,
step a) is carried out at various times, so as to obtain an image of the sample each time;
steps b) to e) are carried out successively using the images obtained at each time.

The method may further comprises emitting a warning when a number of cells considered to be in the apoptosis state exceeds a predetermined value.

In one embodiment:
in step a), an exposure light wave propagates towards the image sensor along a propagation axis;
step c) comprises:
c-i) on the basis of the acquired image, applying a propagation operator, for a plurality of reconstruction distances from the detection plane, so as to estimate, at each reconstruction distance, a complex amplitude of the exposure light wave;
c-ii) on the basis of the complex amplitude estimated, at various reconstruction distances, obtaining a profile representing a variation of the complex amplitude of the exposure light wave along an axis parallel to the propagation axis and passing through the position of the cell;
c-iii) associating each cell with a set of parameters, at least one parameter of the set of parameters depending on the refractive index of the cell or on a relative refractive index of the cell;
c-iv) modelling a cell, taking into account a value of each parameter of the set of parameters, and modelling an exposure light wave, propagating toward the image sensor, under the effect of an illumination, with the light source, of the modelled cell;
c-v) on the basis of the modelled exposure light wave, forming a modelled profile representing a variation in the complex amplitude of the modelled exposure light wave, along an axis parallel to the propagation axis;
c-vi) comparing the profile obtained in c-ii) with the modelled profile resulting from c-v), so as to determine the value of said at least one parameter of the cell;
c-vii) deriving the refractive index of the cell or the relative refractive index of the cell from the parameters associated to the cell.

The at least one parameter of each cell may comprise or depend on the refractive index of the cell or the relative refractive index of the cell.

In one embodiment:
c-iv) comprises modelling cells respectively having various values of refractive index, so as to obtain, following c-v), a database of modelled profiles, each modelled profile being associated with one refractive index;
c-vi) comprises minimizing a deviation between the profile resulting from c-ii) and the modelled profiles of the database, the respective values of the parameters of the cell being those minimizing the deviation.

Steps c-iii) to c-vi) may be implemented iteratively, such that, in each iteration, the profile modelled in c-v) gets gradually closer to the profile obtained in c-ii).

Each iteration may comprise:
determining a deviation between the profile modelled in c-iv) of the same iteration, and the profile obtained in c-ii);
determining a gradient of the deviation as a function of at least one parameter of the set of parameters, so as to determine the values of the parameters of the cell modelled in c-iv) of the following iteration.

In one embodiment:
in step a), an exposure light wave propagates towards the image sensor;
the sample lies in a sample plane;
the sample is described by sets of parameters, each set of parameters being respectively defined at a plurality of radial positions, in the sample plane, each set of parameters comprising at least an optical parameter of the sample, at least one optical parameter being an optical path difference induced by the sample at each radial position step c) comprises:
c-i) taking into account sets of parameters, describing the sample, in the sample plane; c-ii) on the basis of the sets of parameters, forming a complex image of the sample in the sample plane;
c-iii) applying a propagation operator to the complex image formed in c-ii), in order to compute an image of the sample in the detection plane;
c-iv) comparing the image acquired in a) and the image computed in c-iii), in order to compute a validity indicator;
c-v) updating the sets of parameters, so as to make the validity indicator tend toward a preset value;
c-vi) reiterating c-ii) to c-v) taking into account the sets of parameters updated in c-v), until the validity indicator is considered as reaching the preset value;
c-vii) estimating a radial position of a cell;
c-viii) estimating the refractive index or the relative refractive index of the cell from the sets of parameters defined at said at least one radial position of the cell.

c-v) may comprise determining a gradient of the validity indicator as a function of at least one parameter, such that the sets of parameters are updated in order to decrease the validity indicator of the following iteration.

c-v) may comprise updating the sets of parameters, so as to minimize the validity indicator.

c-v) may comprise implementing an algorithm of gradient-descent type.

Each set of parameters may comprise:
at least one optical parameter representative of an optical path difference, along the propagation axis;
an optical parameter representative of absorbance of the cell.

The real part and the imaginary part of the refractive index or of the relative refractive index of a cell may be derived from the optical path difference at radial coordinates corresponding to the cell.

In another embodiment, step c) may comprise
c-i) reconstructing a complex image in the sample plane;
c-ii) selecting a region of interest of the complex image, corresponding to a cell and preferably to a single cell;
c-iii) forming a complex image, called the extracted complex image, from the region of interest selected in c-ii);
c-iv) applying a propagation operator to the extracted complex image resulting from c-iii), in order to obtain, in a propagation plane, a diffraction pattern corresponding to the cell corresponding to the region of interest selected in c-ii);
c-v) estimating the refractive index or the relative refractive index if the cell corresponding to the region of interest selected in c-ii) from the diffraction pattern obtained in c-iv).

Basically, the refractive index or the relative refractive index of a cell may be determined by applying a propagation operator either from the acquired image towards at least one reconstruction plan, and/or from a reconstruction plan towards the detection plan. The reconstruction plan is preferably a plan in which the sample lies.

The invention will be better understood on reading the description of examples of embodiments, which examples are presented, in the rest of the description, with reference to the figures listed below.

FIGURES

FIG. 2A shows the main steps of one embodiment of the invention.

FIG. 2B schematically shows a sequence of substeps relative to a step described with reference to FIG. 2A.

Figure 1:
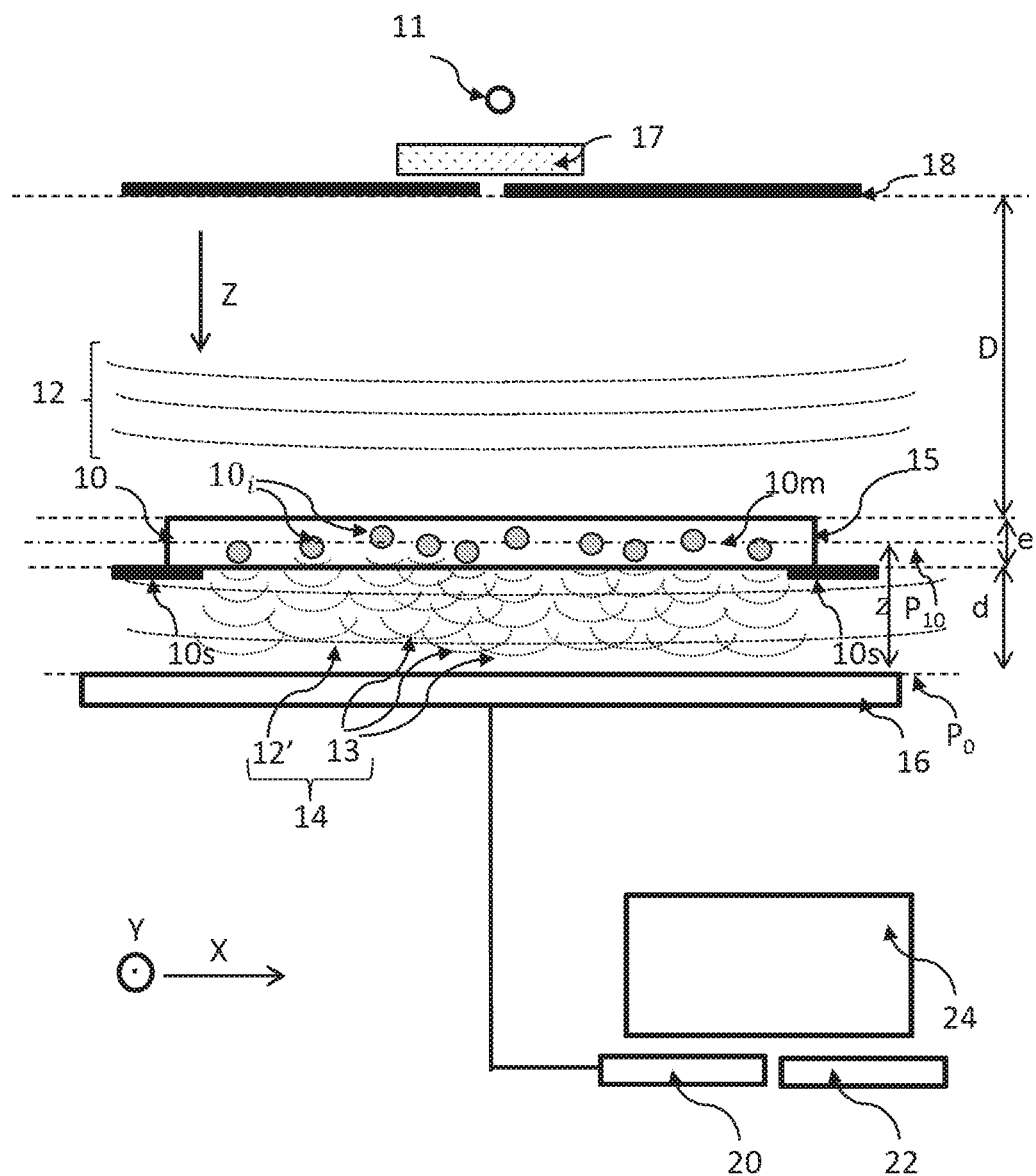
FIG. 1 shows a device allowing the invention to be implemented.
Figure 3A:
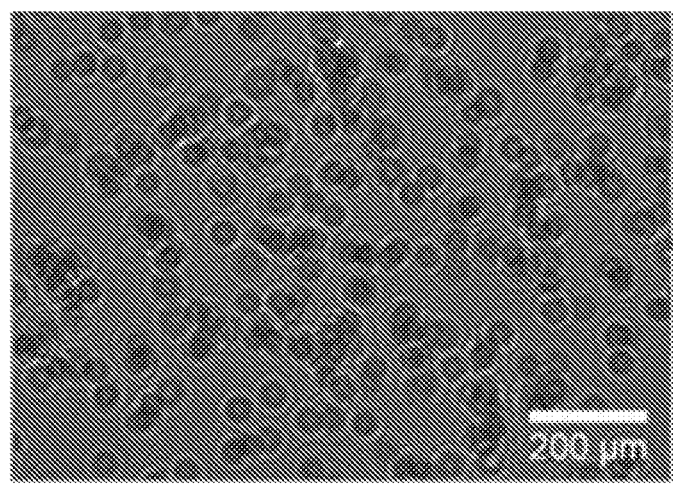

FIG. 3A shows an example of an image of cells, which image was acquired with a device shown in FIG. 1.

Figure 3B:
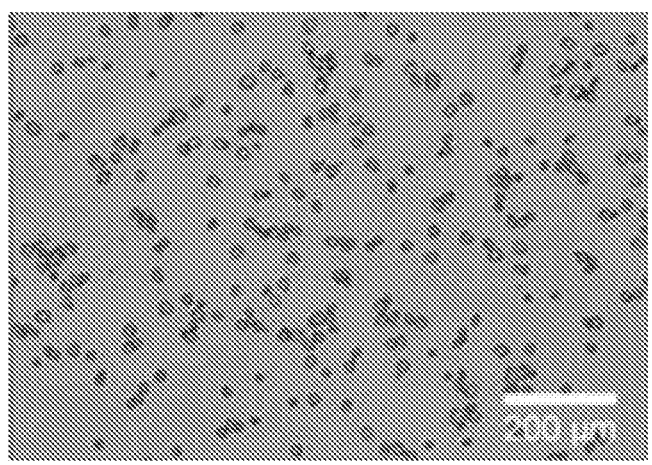

FIG. 3B is a reconstructed modulus image obtained from the image of FIG. 3A.

Figure 3C:
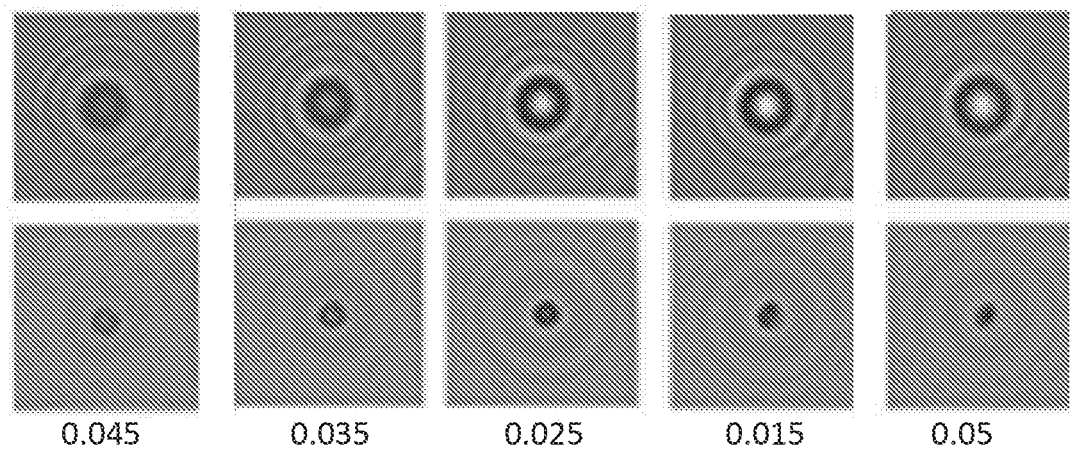

FIG. 3C shows regions of interest extracted from an acquired image (top row) and a reconstructed image (bottom row), respectively, the regions of interest corresponding to cells the relative refractive index of which varies between 0.45 (left-most column) and 0.05 (right-most column).

Figure 4A:
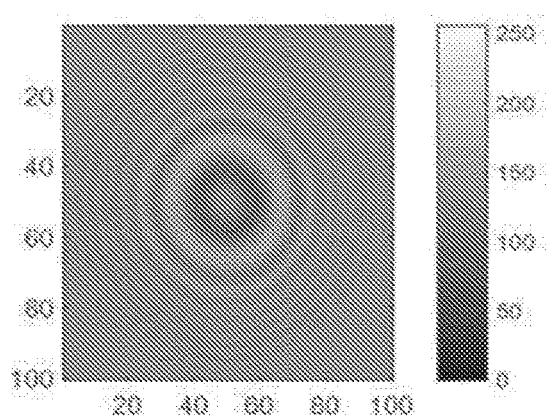
Figure 4B:
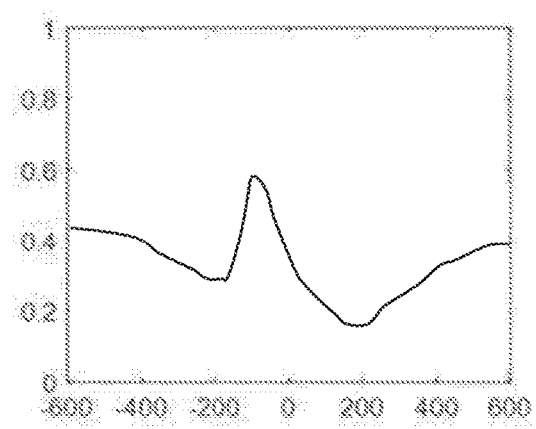

FIGS. 4A and 4B are results of modelling of respectively, a diffraction pattern or profiles corresponding to a cell the parameters of which are known. The same goes for FIGS. 5A and 5B.

Figure 6A:
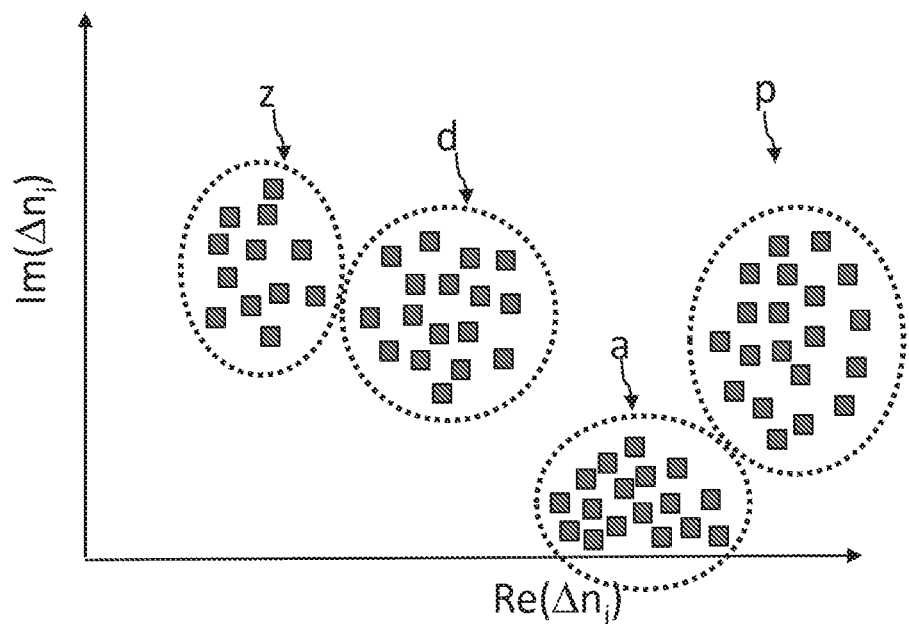

FIG. 6A schematically shows a distribution of the values of the real parts (x-axis) and imaginary parts (y-axis) of relative refractive indices defined for various cells and various states: debris, dead cell, living cell, apoptosis.

Figure 6B:
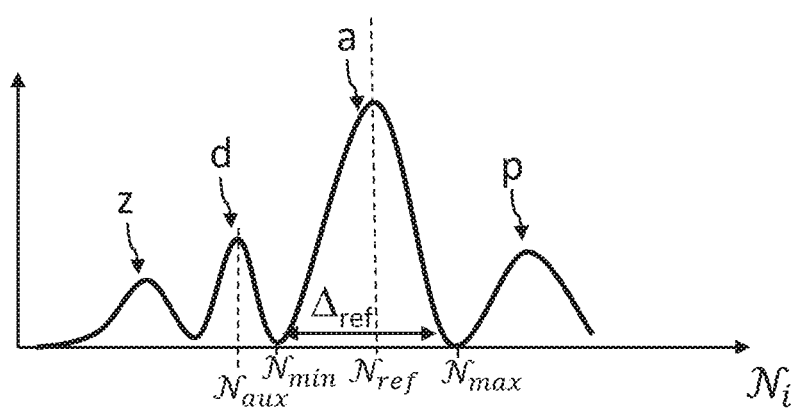

FIG. 6B schematically shows a distribution of the values of an index of interest, for various cells in the states mentioned with reference to FIG. 6A.

Figure 6C:
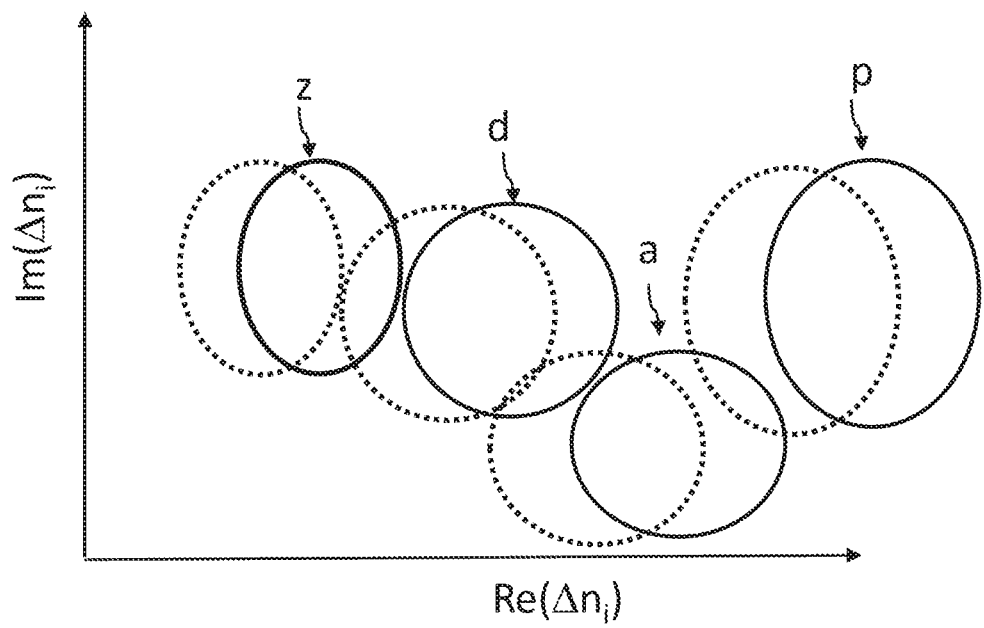

FIG. 6C shows a shift in FIG. 6A, because of a decrease in the refractive index of the culture medium.

Figure 6D:
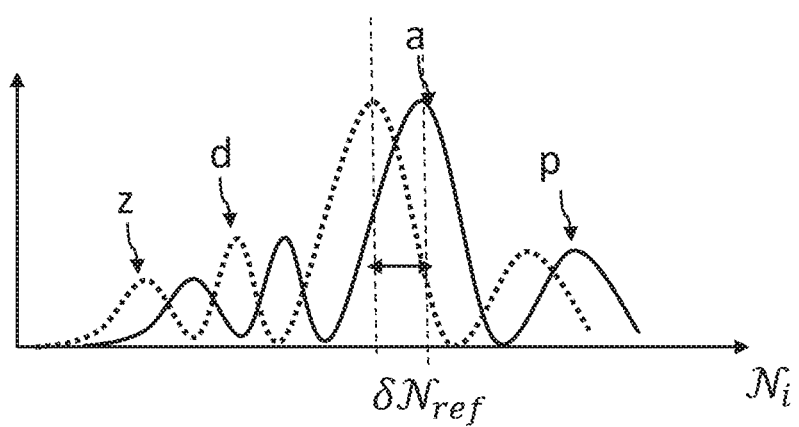

FIG. 6D shows a shift in FIG. 6B, because of a decrease in the refractive index of the culture medium.

Figure 7A:
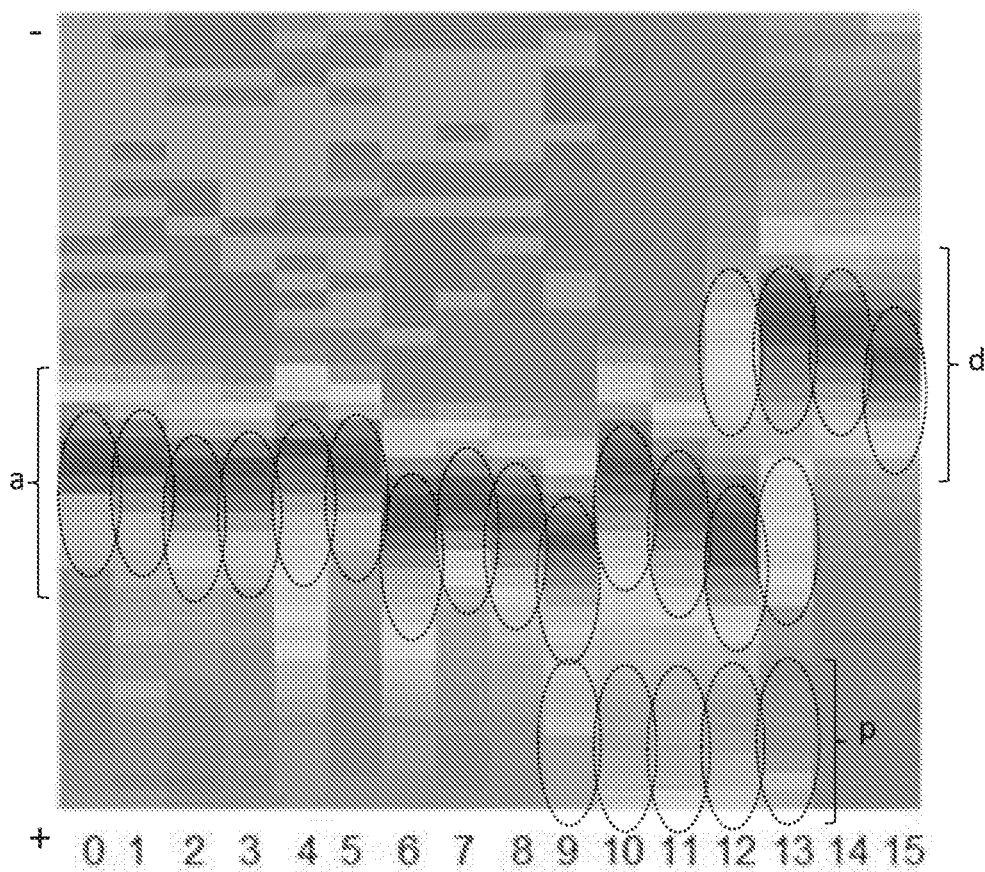

FIG. 7A collates experimentally obtained values of an index of interest, of various cells bathing in a culture medium, as a function of time from inoculation.

Figure 7B:
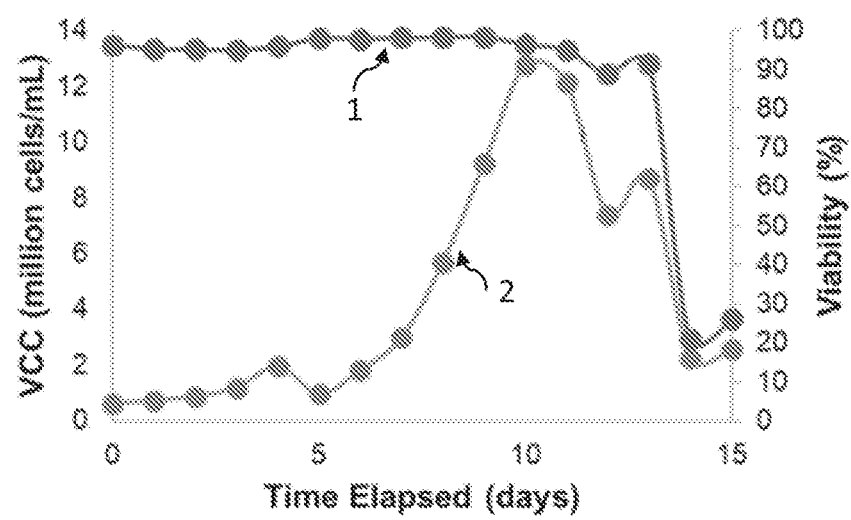

FIG. 7B shows an experimental variation of a viability of cells within a culture medium (y-axis on the right—curve 1) and a variation of a viable cells concentration (VCC) (y-axis to the left—curve 2), as a function of time (x-axis—days).

Figure 7C:
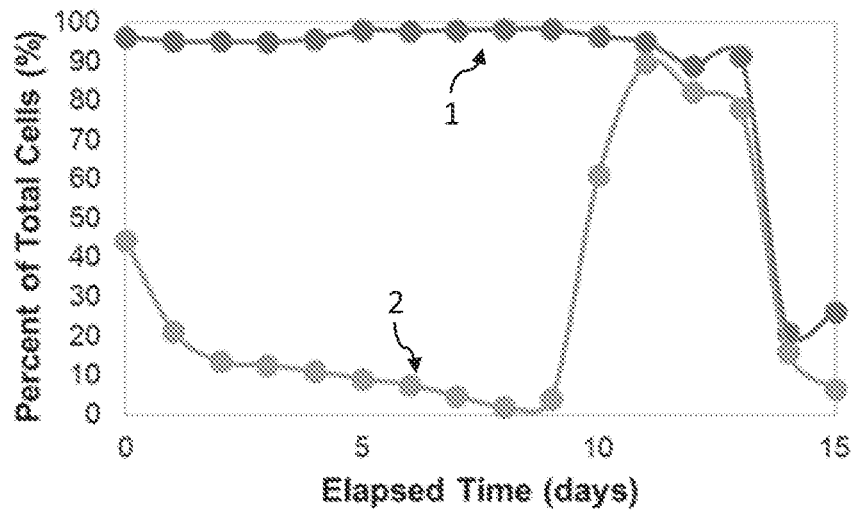

FIG. 7C shows an experimental variation of a viability of cells within a culture medium (curve 1) and a variation of a ratio of cells having a high index of interest (curve 2), as a function of time (x-axis—days).

Figure 8:
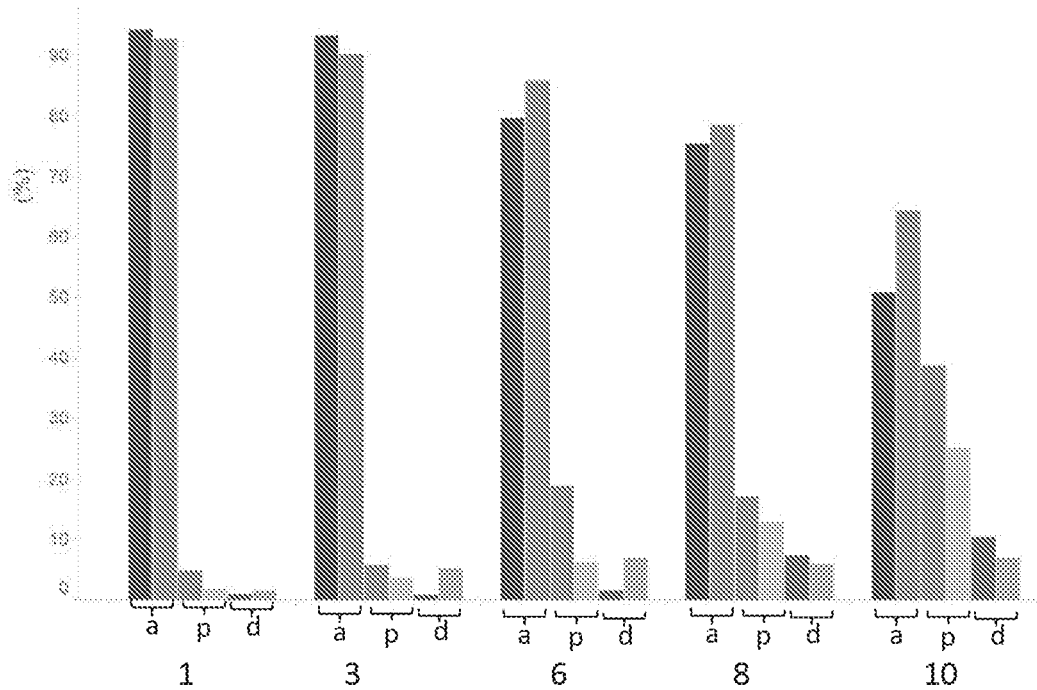

FIG. 8 shows proportions of cellular states estimated by implementing the invention and according to a reference method, as a function of time (x-axis—days).

Figure 9A:
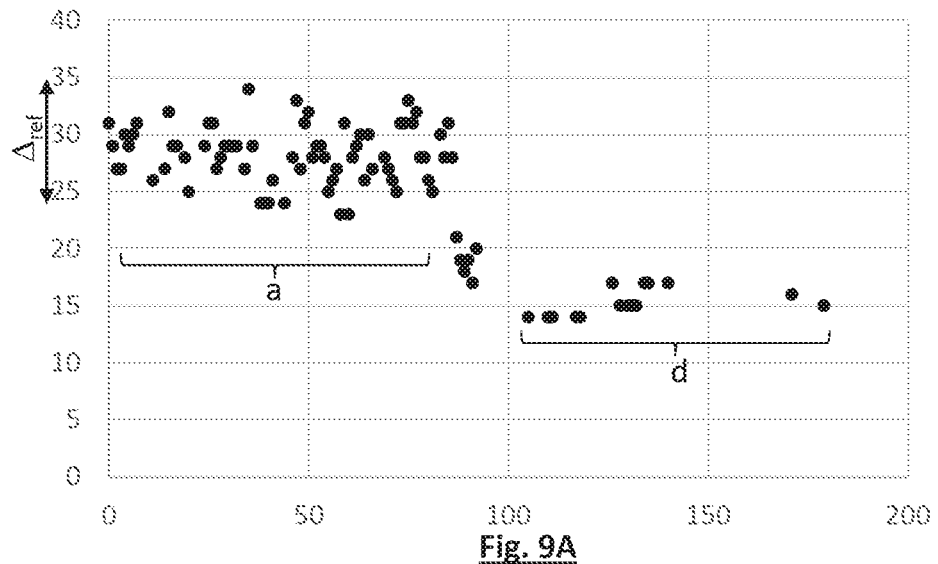
Figure 9B:
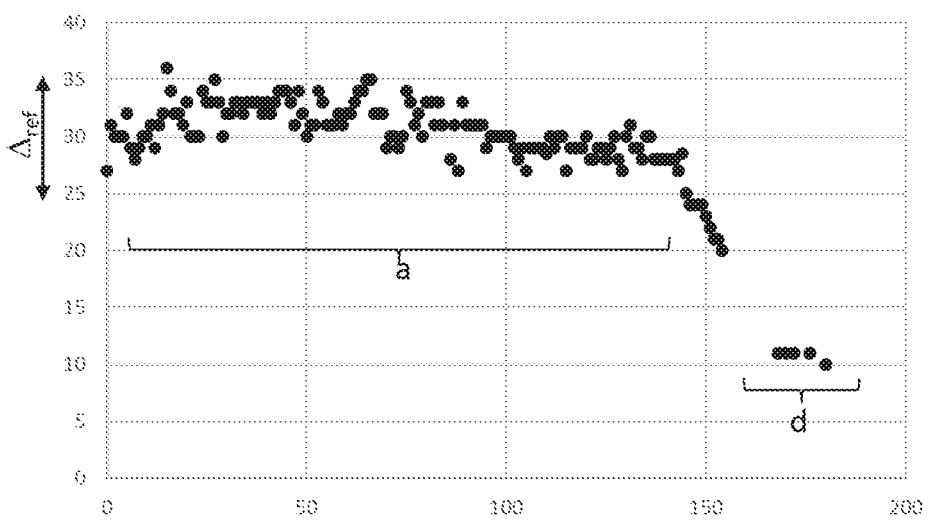

FIGS. 9A and 9B show a variation as a function of time in an index of interest respectively for those cells passing from a living cellular state to the dead cellular state by necrosis.

Figure 9C:
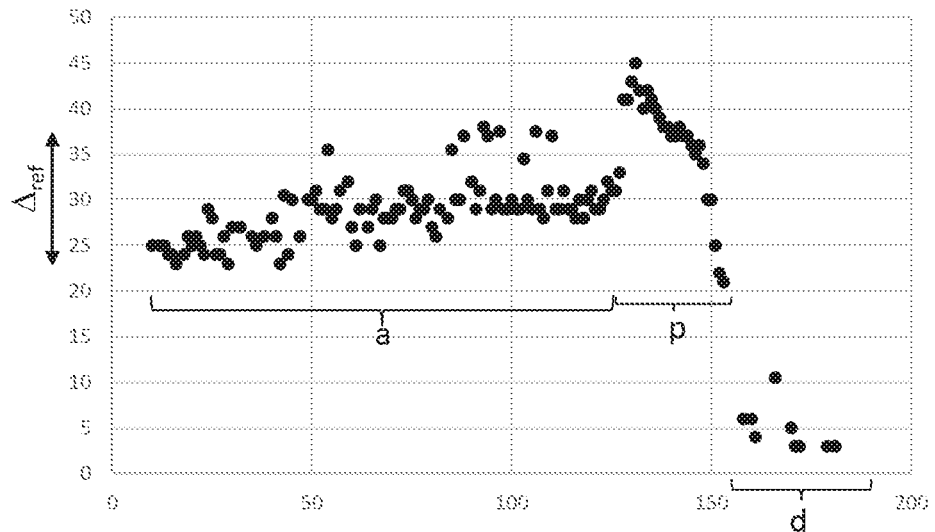
Figure 9D:
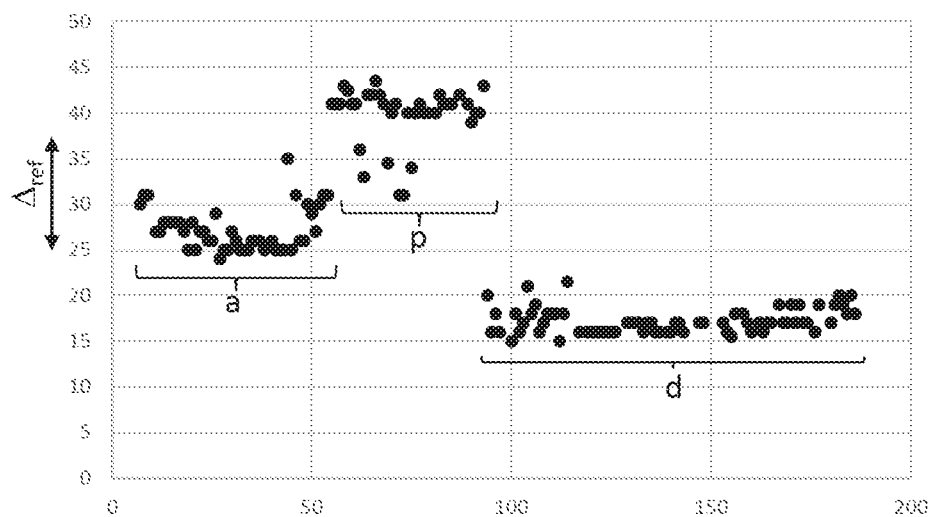

FIGS. 9C and 9D show a variation as a function of time in an index of interest respectively for those cells passing from a living cellular state to the dead cellular state by apoptosis.

Figure 10A:
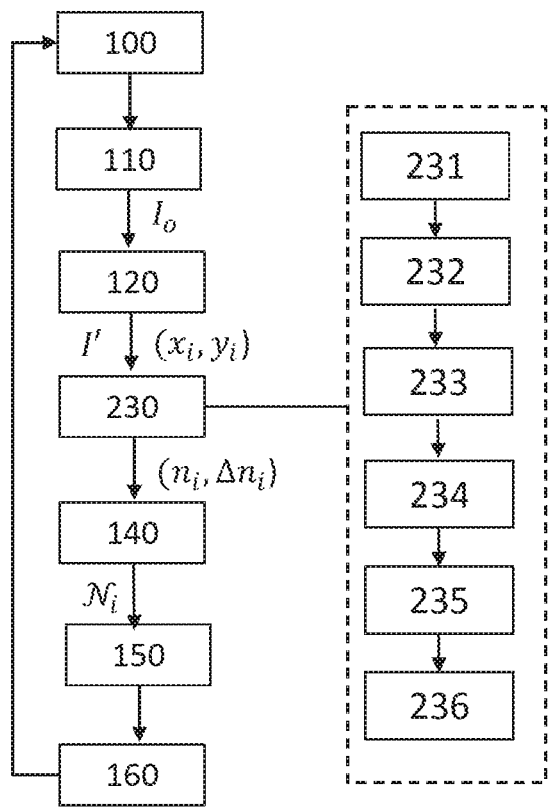

FIG. 10A shows the main steps of a first variant of the invention.

Figure 10B:
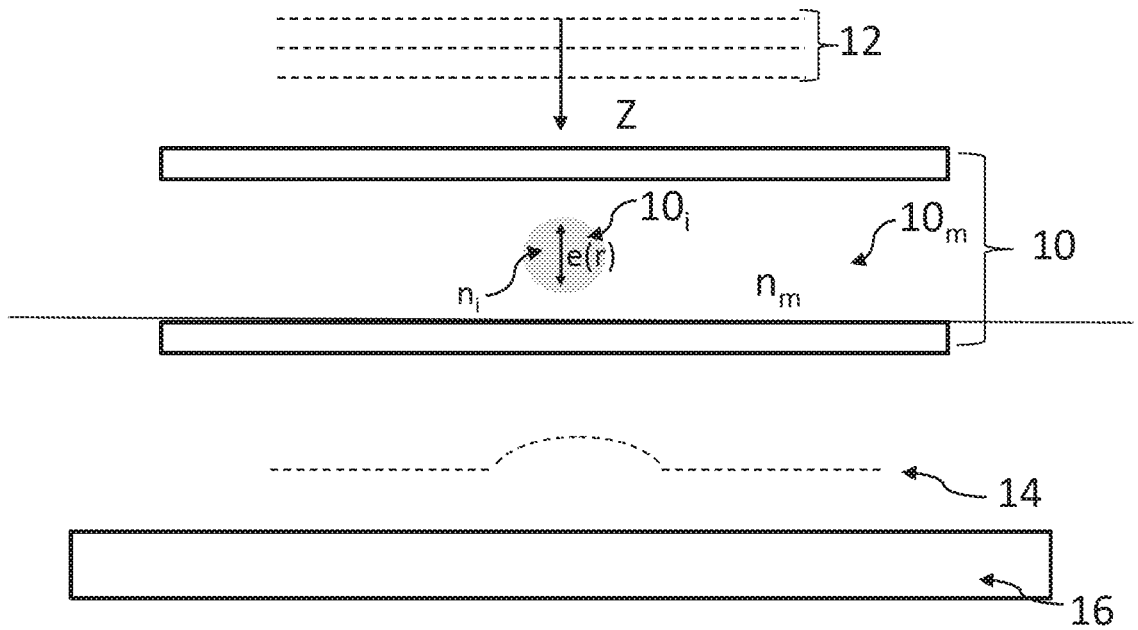

FIG. 10B shows the evolution of a light wave propagating through a cell and illustrates the delay induced by an optical path difference.

Figure 11:
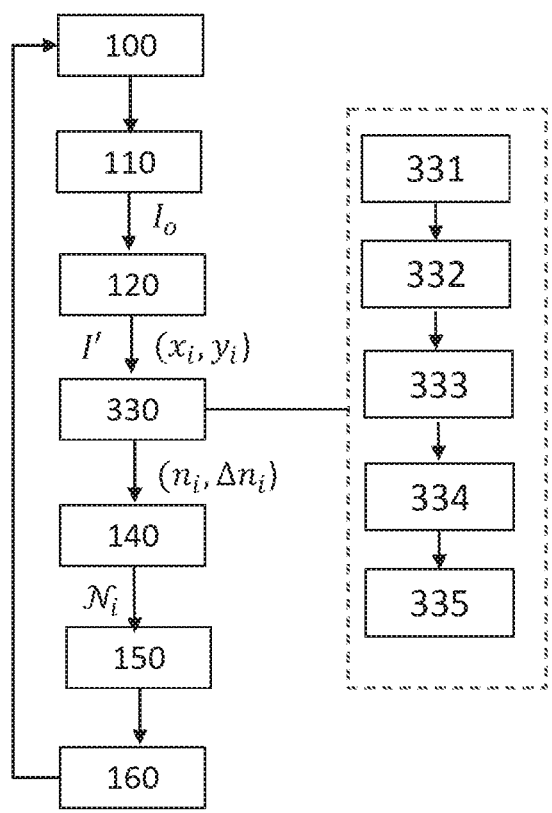

FIG. 11 shows the main steps of another variant of the invention.

Figure 12:
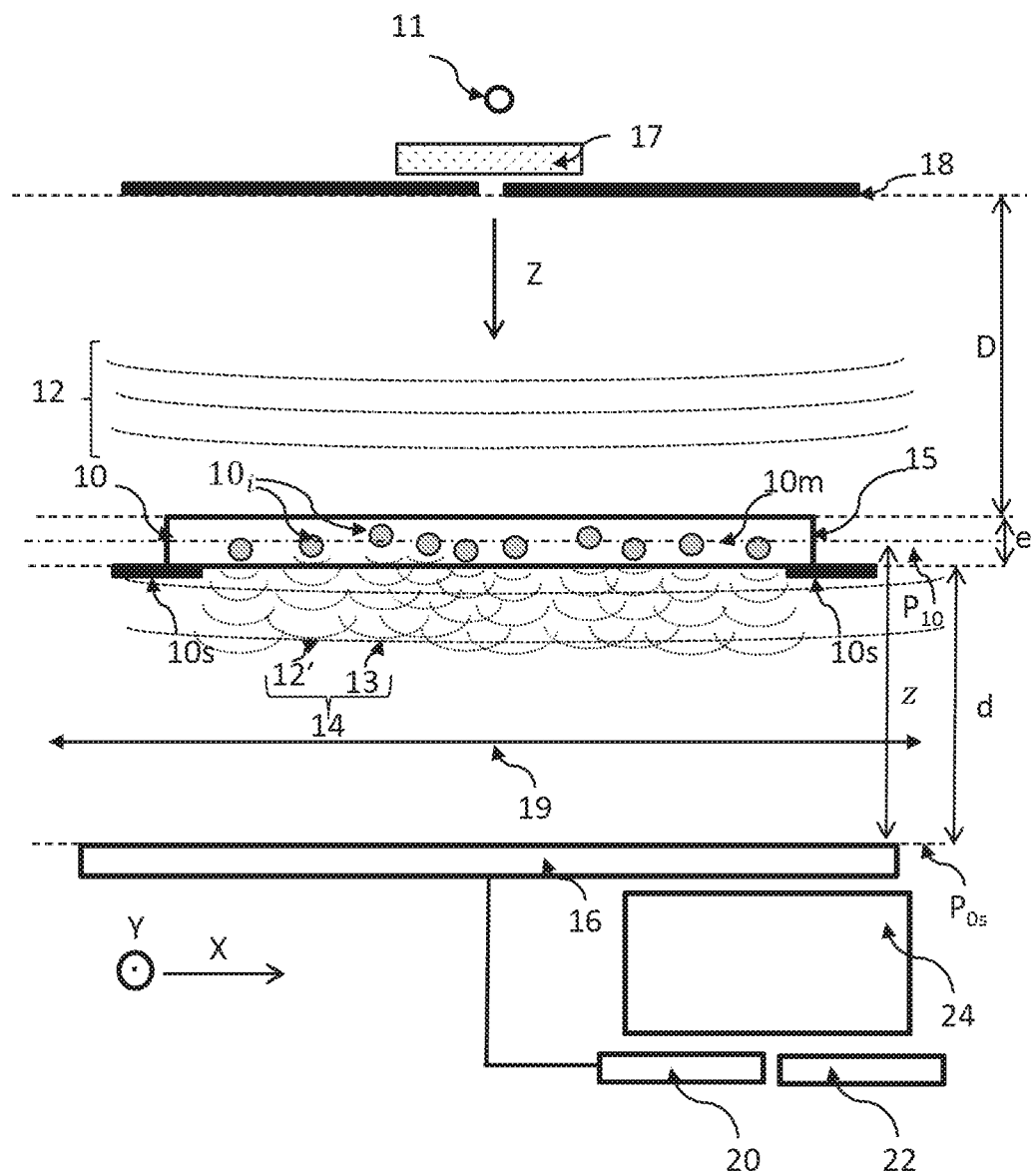

FIG. 12 shows another device allowing the invention to be implemented in a configuration called the defocused-imaging configuration.

DESCRIPTION OF PARTICULAR EMBODIMENTS

FIG. 1 shows an example of a device according to the invention. A light source 11 is configured to emit a light wave 12, called the incident light wave, that propagates in the direction of a sample 10, along a propagation axis Z. The light wave is emitted in an illumination spectral band $\Delta\lambda$.

The sample 10 is a sample that it is desired to characterize. It notably comprises a medium $10m$ in which cells $10_i$ bathe. The medium $10m$ may be a liquid medium, and, in particular, a culture medium, comprising nutrients allowing the development and growth of cells.

The sample 10 is, in this example, contained in a fluidic chamber 15. The fluidic chamber 15 is, for example, a fluidic chamber of thickness e=20 μm. The thickness e of the sample 10, along the propagation axis, typically varies between 10 μm and 1 cm, and is preferably comprised between 20 μm and 500 μm. The sample lies in a plane $P_{10}$, called the sample plane, perpendicular to the propagation axis Z. The sample plane is defined by the axes X and Y shown in FIG. 1. The sample is kept on a holder $10s$ at a distance d from an image sensor 16. The concentration of cells may vary between 1 per microliter and 500 000 per microliter. It may, for example, be equal to 4000 per microliter.

The distance D between the light source 11 and the fluidic chamber 15 is preferably larger than 1 cm. It is preferably comprised between 2 and 30 cm. Advantageously, the light source 11, seen by the sample, may be considered to be point-like. This means that its diameter (or its diagonal) is preferably smaller than one tenth, and better still one hundredth of the distance between the fluidic chamber 15 and the light source. In FIG. 1, the light source is a light-emitting diode. It is generally associated with a diaphragm 18, or spatial filter. The aperture of the diaphragm is typically comprised between 5 μm and 1 mm, and preferably between 50 μm and 500 μm. In this example, the diaphragm is the type of diaphragm supplied by Thorlabs under the reference P150S and its diameter is 150 μm. The diaphragm may be replaced by an optical fiber, a first end of which is placed facing the light source 11 and a second end of which is placed facing the sample 10. The device shown in FIG. 1 also comprises a diffuser 17, placed between the light source 11 and the diaphragm 18. The use of such a diffuser makes it possible to relax constraints on the centrality of the light source 11 with respect to the aperture of the diaphragm 18. The function of such a diffuser is to distribute the light beam produced by an elementary light source 11 into a cone of angle α. Preferably, the scattering angle α varies between 10° and 80°. Alternatively, the light source may be a laser source, such as a laser diode. In this case, it is not useful to associate therewith a spatial filter or a diffuser.

Preferably, the emission spectral band $\Delta\lambda$ of the incident light wave 12 has a width smaller than 100 nm. By spectral bandwidth, what is meant is a fullwidth at half maximum of said spectral band.

The sample 10 is placed between the light source 11 and the aforementioned image sensor 16. The image sensor 16 defines a detection plane $P_0$, which preferably lies parallel, or substantially parallel, to the plane $P_{10}$ in which the sample lies. The term substantially parallel means that the two elements may not be rigorously parallel, an angular tolerance of a few degrees, smaller than 20° or 10°, being acceptable.

The image sensor 16 is configured to form an image $I_0$ of the sample 10 in the detection plane $P_0$. In the example shown, it is a question of a CCD or CMOS image sensor 16 comprising a matrix array of pixels. The detection plane $P_0$ preferably lies perpendicular to the propagation axis Z of the incident light wave 12. The distance d between the sample 10 and the matrix array of pixels of the image sensor 16 is preferably comprised between 50 µm and 2 cm, and preferably comprised between 100 µm and 2 mm.

The absence of magnifying or image-forming optics between the image sensor 16 and the sample 10 in this embodiment will be noted. This does not prevent focusing micro-lenses potentially being present level with each pixel of the image sensor 16, said micro-lenses not having the function of magnifying the image acquired by the image sensor, their function rather being to optimize light detection performance. One advantage of such an embodiment is that it allows cells located facing a detection area able to reach 10 mm² or a few tens of mm² to be addressed simultaneously. Contrary to a microscopy- or cytometry-type device, this allows a high number of cells to be addressed simultaneously.

The light source 11 may comprise elementary light sources, emitting in the various spectral bands. The image sensor is then configured to acquire, simultaneously or successively, an image $I_0$ in each spectral band.

As mentioned in the patent application U.S. Pat. No. 10,481,076 cited with respect to the prior art, under the effect of the incident light wave 12, the cells $10_i$ present in the sample may generate a diffracted wave 13, liable to produce, in the detection plane $P_0$, interference, in particular, with a portion 12' of the incident light wave 12 transmitted by the sample. Moreover, the sample may absorb a portion of the incident light wave 12. Thus, the light wave 14, transmitted by the sample, and to which the image sensor 16 is exposed, designated by the term "exposure light wave", may comprise:

- a component 13 resulting from the diffraction of the incident light wave 12 by each cell of the sample;
- a component 12' resulting from the transmission of the incident light wave 12 by the sample, a portion of the latter possibly being absorbed in the sample.

These components form interference in the detection plane. Thus, each image acquired by the image sensor comprises interference patterns (or diffraction patterns), each interference pattern possibly being associated with a cell $10_i$ of the sample.

A processor 20, for example, a microprocessor, is configured to process each image $I_0$ acquired by the image sensor 16. In particular, the processor is a microprocessor connected to a programmable memory 22 in which a sequence of instructions for performing the image-processing and computing operations described in this description is stored. The processor may be coupled to a screen 24 allowing the display of images acquired by the image sensor 16 or computed by the processor 20.

Generally, from each acquired image, the microprocessor is programmed to locate and estimate an amount (number or concentration) of cells $10_i$ present in the field of observation, and to estimate an index of interest, of each located cell. From the index of interest, it is possible to determine a state of the cell $10_i$ among predetermined states. The predetermined states are notably chosen from a living state, a necrotic state (cell death), and an apoptotic state. The apoptotic state corresponds to a transitional state, entered by the cell during apoptosis, prior to cell death.

The method may comprise computing a viability from an amount of living cells relative to an amount of cells that are either dead or in apoptosis, or to all the cells counted in the acquired image.

FIG. 2A shows the main steps of a method according to the invention, according to a first embodiment.

Step 100: Illuminating the sample 10 using the light source 11.

Step 110: Acquiring an image $I_0$ of the sample 10 with the image sensor 16, this image forming a hologram.

Step 120: Detecting cells $10_i$ in the sample. The acquired image $I_0$ generally contains a high number of interference patterns. Because of the overlap between the various interference patterns, the acquired image is generally not easily usable to locate the cells $10_i$ present in the observed field. The latter are more easily identifiable in a complex image reconstructed by applying a propagation operator h to the acquired image $I_0$.

An image $I_0$ acquired by the image sensor 16, also called a hologram, may be the subject of a reconstruction, called a holographic reconstruction. As described with reference to the prior art, it is possible to apply, to the image acquired by the image sensor, a propagation operator h, so as to compute a complex amplitude A(x, y, z) representative of the exposure light wave 14, and to do so at any point of spatial coordinates (x, y, z), and more particularly between the image sensor and the sample. The coordinates (x, y) designate coordinates, called radial coordinates, parallel to the detection plane $P_0$. The coordinate z is a coordinate along the propagation axis Z, expressing a distance between the sample 10 and the image sensor 16.

The complex amplitude may be obtained via one of the following expressions:

$A(x,y,z)=I_0(x,y,z)*h$, * designating the convolution operator, or, and preferably, $A(x,y,z)=\sqrt{I_0(x,y,z)}*h$, or indeed:

$$A(x, y, z) = \frac{\sqrt{I_0(x, y, z)}}{\bar{I}_0} * h,$$

$\bar{I}_0$ being an average of the acquired image.

The function of the propagation operator h is to describe the propagation of light between the image sensor 16 and a point of coordinates (x, y, z) located at a distance |z| from the image sensor.

It is then possible to determine a property of the exposure light wave 14, for example, the modulus M(x, y, z) and/or the phase φ (x, y, z), at the distance |z| with:

$M(x,y,z)=\text{abs}[A(x,y,z)];$ $\varphi(x,y,z)=\arg[A(x,y,z)];$

The operators abs and arg designate the modulus and argument, respectively.

The distance |z| is a reconstruction distance.

The propagation operator is, for example, the Fresnel-Helmholtz function, such that:

$$h(x, y, z) = \frac{1}{j\lambda z} e^{j2\pi \frac{z}{\lambda}} \exp\left(j\pi \frac{x^2 + y^2}{\lambda z}\right).$$

The complex expression A(x, y, z) of the light wave 14, at any point of spatial coordinates (x, y, z), is such that: $A(x, y, z)=M(x, y, z)e^{j\varphi(x,y,z)}$.

The complex expression A is a complex quantity the argument and modulus of which are respectively representative of the phase and intensity of the exposure light wave 14 detected by the image sensor 16 in order to form the image $I_0$.

By determining the complex amplitude, for a given radial position (x, y), along the Z-axis, at a plurality of coordinates z, it is possible to form a profile representative of the exposure light wave. It may be a question of a profile of the phase or of the modulus of the exposure light wave. Generally, it is a question of a profile of an optical property of the exposure light wave, the term optical property designating a property obtained using the complex amplitude A(x, y, z), and representative of the latter. It may be a question of the modulus, of the phase, of the real part, of the imaginary part, or of combinations thereof.

According to one embodiment, the image $I_0$ is convoluted with the propagation operator h. This allows a complex image $A_z$ representing a spatial distribution of the complex expression A in a reconstruction plane $P_z$, lying at a distance |z| from the detection plane $P_0$, to be obtained. In this example, the detection plane $P_0$ has the equation z=0. The complex image $A_z$ corresponds to a complex image of the sample in the reconstruction plane $P_z$. It also represents a two-dimensional spatial distribution of the optical properties of the exposure light wave 14. Such a method, designated by the term holographic reconstruction, notably allows an image of the modulus or of the phase of the exposure light wave 14 in the reconstruction plane to be reconstructed.

It is possible to form images $M_z$ and $\varphi_z$ respectively representing the modulus or phase of a complex image $A_z$ in a plane $P_z$ located at a distance |z| from the detection plane $P_0$, with $M_z$=mod ($A_z$) and $\varphi_z$=arg ($A_z$). When the reconstruction plane corresponds to the sample plane $P_{10}$, the images $M_z$ and $\varphi_z$ allow the sample to be observed with a correct spatial resolution.

Step 120 comprises reconstructing at least one image, called the observation image I', of the sample from the image $I_0$. The observation image I' may be obtained by applying a propagation operator h to the acquired image $I_0$, for a reconstruction distance, so as to obtain a complex image $A_z$ representing the complex amplitude of the exposure light wave 14 in a reconstruction plane parallel to the detection plane and located at the reconstruction distance from the latter.

The observation image I' may be the image of the modulus or of the phase of the complex image $A_z$ thus reconstructed, or the image of the real part or of the imaginary part of such a complex image. The reconstruction plane in which the observation image is defined is preferably the sample plane $P_{10}$. Its position may be set beforehand, or determined using a numerical focusing algorithm, this type of algorithm being known to those skilled in the art.

The observation image I' may also be formed using an iterative holographic reconstruction algorithm, such as described in WO2016189257 or in WO2017162985. In such algorithms, the phase of the exposure light wave, in the detection plane, is gradually adjusted. In WO2016189257, the phase is adjusted iteratively by averaging, in each iteration, the phase of light waves reconstructed in the sample plane, in various spectral bands. In WO2017162985, the phase is adjusted iteratively so as to minimize, in each iteration, the reconstruction noise of a complex image reconstructed in the sample plane.

In the observation image I', the cells $10_i$ appear sufficiently contrasted to be easily discernible from the ambient medium 10m.

It is possible to apply a segmentation or morphology-analysing algorithm to the observation image, so as to detect cells in the observation image, and to attribute, to each detected cell, a radial coordinate ($x_i$, $y_i$), corresponding to each cell $10_i$ detected in the observation image I' or on the acquired image $I_0$. By radial coordinate, what is meant is a coordinate in a plane parallel to the detection plane $P_0$.

FIG. 3A is an example of an image $I_0$ of a cell-containing sample acquired by the image sensor. FIG. 3B is an observation image I' obtained by applying, to the image of FIG. 3A, a holographic reconstruction algorithm such as described in WO2017162985.

Step 120 may be carried out in other ways, such as described below.

Step 130: Determining the refractive index $n_i$ or the relative refractive index $\Delta n_i$ of each detected cell $10_i$.

Step 130 may be achieved according to the method described in the French patent application FR1859362 (or U.S. Ser. No. 16/595,661), and more precisely following steps 130 to 150 of the latter. Those steps are summarized hereafter.

The objective of step 130 is to determine a relative refractive index of each cell $10_i$ detected in step 120. The relative refractive index $\Delta n_i$ is a comparison, taking the form of a difference or a ratio, between the refractive index $n_i$ of a cell $10_i$ and the refractive index $n_m$ of the culture medium 10m.

The inventors have demonstrated that the hologram of a cell $10_i$, corresponding to a diffraction pattern of the image $I_0$ acquired by the image sensor, varies as a function of the relative refractive index $\Delta n_i$ of the cell. The same goes for the trace of said cell in the observation image I'. FIG. 3C shows, in the top row, various holograms corresponding to a CHO cell (Chinese hamster ovary cell) of given size and of relative index $\Delta n_i$ varying between 0.045 (left-most column) and 0.005 (right-most column). It may clearly be seen that the appearance of the hologram varies significantly as a function of the refractive index. FIG. 3C shows, in the bottom row, modulus images respectively reconstructed from each hologram.

FIG. 3C shows that a small variation in the relative index $\Delta n_i$ of a cell $10_i$ leads to an easily detectable variation in the hologram of the cell or in a reconstruction image established from said hologram.

In a first embodiment, step 130 comprises three substeps.

Substep 131: in this substep, for each detected cell, a profile $F_{x_i,y_i}$ representative of a complex amplitude of the exposure light wave 14 is established along the axis of propagation Z of the light, at least between the cell $10_i$ and the image sensor 16. $x_i$ and $y_i$ are the radial coordinates of the cell $10_i$ within the detection plane. The profile corresponds to a variation, parallel to the axis of propagation Z, of a quantity established from the complex amplitude A of the exposure light wave 14. It may be the modulus, or the phase, or the real part, or the imaginary part. Use of such profiles has been described in U.S. Pat. No. 10,481,076.

According to one option, this step may comprise forming complex images $A_z$ for various reconstruction distances. Thus, a stack of complex images $A_{z_1} \ldots A_{z_n}$ is obtained, each complex image being defined, in the radial coordinates (x, y), respectively at reconstruction distances $z_1 \ldots z_n$ with respect to the detection plane. Each complex image $A_z$ of the stack of images $A_{z_1} \ldots A_{z_n}$ corresponds to one reconstruction distance z. On the basis of the value of each complex image at a radial coordinate ($x_i$, $y_i$), corresponding to one cell $10_i$ it is possible to obtain the value of an optical property for the various reconstruction distances, the interpolation of which allows a profile $F_{x_i,y_i}$ to be formed. When the optical property in question is the modulus, the profile $F_{x_i,y_i}$ is noted $M_{x_i,y_i}$. When the optical property in question is the phase, the profile $F_{x_i,y_i}$ is noted $\varphi F_{x_i,y_i}$. The profile corresponds to a variation of the optical property along an axis parallel to the propagation axis Z, and passing through the radial coordinate $(x_i, y_i)$ of the cell $10_i$.

The complex images $A_{z_1} \ldots A_{z_n}$ may be formed using an iterative holographic reconstruction algorithm, such as described in WO2016189257 or in WO2017162985. With such algorithms, the phase of the exposure light wave in the detection plane is gradually adjusted. In WO2016189257, the adjustment of the phase is achieved iteratively, the phase of light waves reconstructed in the sample plane, in various spectral bands, being averaged in each iteration. In WO2017162985, the adjustment of the phase is achieved iteratively so as to minimize, in each iteration, the reconstruction noise of a reconstructed complex image in the sample plane.

According to one option, described in WO2017178723, a stack of complex images $A_{z_1} \ldots A_{z_n}$ is obtained by applying an iterative reconstruction algorithm to an image $I_0$ acquired by the image sensor 16. The iterative algorithm is applied so as to reconstruct a complex image, called the reference complex image $A_{10}$, in the plane $P_{10}$ of the sample. It is assumed that the reference complex image $A_{10}$ forms a good descriptor of the exposure light wave 14. It, in particular, comprises reliable estimations of the modulus and phase of the exposure light wave 14 in the plane $P_{10}$ of the sample. The other complex images forming the stack of images $A_{z_1} \ldots A_{z_n}$ are obtained by simply convoluting the reference complex image $A_{10}$ with a propagation operator h such as described above.

According to another option, each complex image $A_z$ of the stack of images $A_{z_1} \ldots A_{z_n}$ is obtained by successive application of an iterative reconstruction algorithm to the image $I_0$ acquired by the image sensor, various reconstruction distances $z_1 \ldots z_n$ being considered.

It is not necessary to use a stack of complex images to establish a profile $F_{x_i,y_i}$. A profile $F_{x_i,y_i}$ may be obtained by estimating the complex amplitude $A(x_i, y_i, z)$ of the exposure light wave at various coordinates z, for given radial coordinates $(x_i, y_i)$, on the basis of one acquired image $I_0$ or of a plurality of images acquired in different spectral bands.

Substep 132: obtaining modelled profiles.

Substep 132 comprises using modelled profiles established on the basis of modelled cells 10(par). To do this, a set of parameters par of a cell is taken into account. Then, via a numerical model, the complex amplitude of an exposure light wave $14_{mod}$, propagating between the modelled cell and the image sensor 16, and resulting from an illumination of the modelled cell 10(par) with the light source 11, is modelled.

The model may notably be based on Mie scattering. Mie scattering is a model of elastic scattering allowing a solution to be obtained to Maxwell's equations, describing a light wave diffracted by a spherical cell illuminated by a monochromatic incident light wave of wavelength λ. Apart from its spherical shape, a cell $10_i$ is characterized by a refractive index $n_i$, the latter possibly notably being a complex refractive index $n_i = \text{Re}(n_i) + j\text{Im}(n_i)$, with $j^2 = -1$. Re et Im are operators that return the real part and imaginary part, respectively. Each cell $10_i$, may also be characterized by a relative refractive index $\Delta n_i$, the latter possibly notably being a complex relative refractive index $\Delta n_i = \text{Re}(\Delta n_i) + j\text{Im}(\Delta n_i)$.

Thus, the set of parameters par of a cell $10_i$, comprises at least the refractive index $n_i$ or the relative refractive index $\Delta n_i$. In the described embodiment, the relative refractive index $\Delta n_i$ is considered. When the relative refractive index $\Delta n_i$ is expressed in the form of a complex quantity, the parameters comprise the real part $\text{Re}(\Delta n_i)$ of the refractive index and its imaginary part $\text{Im}(\Delta n_i)$. As indicated above, the parameters par assigned to a cell $10_i$, may further comprise a dimension (diameter or radius) and/or a distance z of the cell with respect to the detection plane, along the propagation axis Z.

Figure 5A:
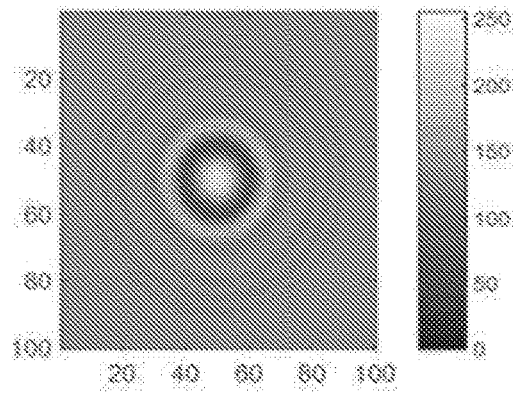

The application of the Mie-scattering model allows a diffraction pattern $I_{mod}(\text{Par})$ to be simulated at various distances from the sample. This notably allows a diffraction pattern $I_{0,mod}(\text{par})$ to be formed in the detection plane $P_0$, as shown in FIGS. 4A and 5A. The notation $I_{0,mod}(\text{par})$ designates the fact that the diffraction pattern is modelled in the detection plane $P_0$, as a function of a set of parameters par. The set of parameters par may form a vector of parameters, in the sense that the set of parameters may be represented in vector form.

FIG. 4A is of a diffraction pattern $I_{0,mod}(\text{par})$, in the detection plane, resulting from the diffraction of a light wave of 450 nm wavelength, by a modelled cell 10(par) the diameter of which is equal to 15 μm, and propagating through a medium of index equal to 1.33, and then through air between the medium to the image sensor 16. The refractive index n of the modelled cell is 1.37, i.e. relative index Δn equal to 0.04 with respect to the index of the medium. In these figures, the imaginary part Im(Δn) of the relative refractive index has been considered to be zero. The distance between the image sensor 16 and the modelled cell 10(par) was considered to be equal to 1000 μm.

In order to take into account the imperfections of the image sensor 16, the modelled diffraction patterns have been spatially sampled considering a pixel pitch, the latter being, in this example, equal to 1.67 μm. The patterns were then blurred by applying a Gaussian filter in order to take into account the coherence of the light source 11.

The pattern of FIG. 4A was obtained by modelling, in the detection plane $P_0$, the complex amplitude $A(x, y, z)$ of the exposure light wave $14_{mod}$ propagating toward the detection plane, the modelled exposure light wave resulting from the illumination of the modelled cell. The modulus of the complex amplitude $A(x, y, z)$, in the detection plane $P_0$, was then extracted so as to make it possible to simulate the diffraction pattern formed in the image acquired by the image sensor.

From the modelled diffraction pattern $I_{0,mod}(\text{par})$, it is possible to form a profile, called the modelled profile F(par), representing a variation, parallel to the propagation axis Z, of the complex amplitude $A(x, y, z)$ of the modelled exposure light wave $14_{mod}$. The modelled profile F(par) is preferably established, from the modelled diffraction pattern $I_{0,mod}$, in the same way as the profile $F_{x_i,y_i}$ was established from the acquired image $I_0$. When the profile $F_{x_i,y_i}$ was established by forming a stack of complex images from the acquired image $I_0$, the modelled profile F(par) is established by forming a stack of complex images $A_{z_1,mod} \ldots A_{z_n,mod}$ from the modelled diffraction pattern $I_{0,mod}$. The modelled profile F(par) represents a model of the variation in the complex amplitude $A_{mod}(x, y, z)$ of the modelled exposure light wave $14_{mod}$, and passing through a determined radial position. The radial position may notably correspond to the centre of the diffraction pattern, this also corresponding to the coordinates of the centre of the modelled cell in a plane parallel to the detection plane.

FIG. 4B is a modelled profile F(par) of the modulus of the modelled complex expression $A_{mod}(x, y, z)$, passing through a radial coordinate (x, y) located at the centre of a modelled cell 10(par), the diameter of which is equal to 15 μm. A distance of 1000 μm between the image sensor and the modelled cell has been considered. In the graphs, the abscissa 0 corresponds to the position of the cell. The unit of the abscissa axis is µm.

FIG. 5A is a simulation of a diffraction pattern $I_{0,mod}(par)$ resulting from the diffraction of a light wave of 450 nm wavelength, by a modelled cell the diameter of which is equal to 15 µm, propagating through a medium of index equal to 1.33, and then through air between the medium to the image sensor. The refractive index n of the cell is 1.34, i.e. a relative index $\Delta n$ equal to 0.01. In this figure, a distance of 1000 µm between the image sensor and the modelled cell has been considered FIG. 5B is a modelled profile F(par) of the modulus of the modelled complex expression, passing through a radial coordinate (x, y) located at the centre of a modelled cell 10(par), the diameter of which is equal to 15 µm.

Figure 5B:
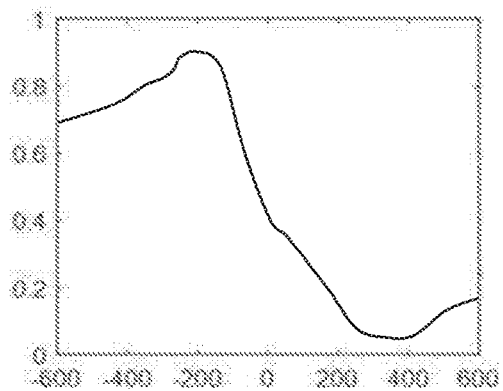

Comparison of FIGS. 4B and 5B shows that, for a given cell size, a small variation in relative refractive index has a substantial influence on the profile.

FIGS. 4A, 4B, 5A and 5B show that it is possible to model the complex amplitude of the exposure light wave 14 to which the image sensor 16 is exposed. This, in particular, allows profiles F(par), for example, profiles of modulus or of phase, corresponding to cells the parameters (size, refractive index n) of which are known to be modelled numerically. More generally, the model allows a profile F(par), representative of the complex amplitude of the exposure light wave, to be established for a cell the parameter, or the parameters par, of which are known.

The parameters of the cell form a set par that may comprise:
- a refractive index n of the cell, this index possibly being a complex quantity, or a relative refractive index $\Delta n$;
- and/or a dimension of the cell, of the radius r or diameter d type;
- and/or a distance z of the cell with respect to the detection plane.

Each modelled profile also depends on wavelength $\lambda$.

Thus, substep 132 comprises:
- modelling a diffraction pattern $I_{0,mod}$ in the detection plane;
- to the modelled diffraction pattern, applying a numerical reconstruction algorithm in order to establish a profile F(par), parallel to the propagation axis Z, of a complex amplitude $A_{mod}(x, y, z)$ of a modelled exposure light wave $14_{mod}$.

Alternatively, the modelled profiles may be obtained without necessarily modelling a diffraction pattern $I_{0,mod}$ in the detection plane. The complex amplitude of the exposure light wave $14_{mod}$ along the propagation axis Z is then modelled. However, the inventors believe that it is preferable to model the diffraction pattern $I_{0,mod}(par)$, then to form the profile F(par) corresponding to the modelled cell in the same way as a profile $F_{x_i,y_i}$ passing through a coordinate ($x_i$, $y_i$), is formed, on the basis of the image $I_0$ acquired by the image sensor.

Whatever the way in which they are obtained, the profiles F(par) thus modelled may be stored in a database, so as to be exploited in a method the main steps of which are described below. Each profile is associated with a set of parameters (par).

Substep 133: Comparing the profile $F_{x_i,y_i}$ formed for each cell with modelled profiles F(par), each modelled profile being parameterized by a set of parameters par as mentioned above. Substep 133 comprises determining the modelled profile F*(par) closest to the profile $F_{x_i,y_i}$ formed for the cell. The parameters $par_i$ of the cell $10_i$ are the parameters associated with the closest modelled profile F*(par).

According to one option, substep 133 comprises comparing the profile $F_{x_i,y_i}$ to each modelled profile F(par), so as to determine the parameters of the profile minimizing the comparison. The comparison may, for example, comprise a squared deviation, in which case:

$$par_i = \arg\min_{par}[F_{x_i,y_i} - F(par)]^2$$

According to another option, illustrated in FIG. 2B, it is possible to apply an iterative algorithm allowing a profile F(par) closest to the measured profile $F_{x_i,y_i}$ to be estimated. In this embodiment, the set of parameters par of the modelled cell is gradually adjusted such that the profile F(par) corresponding to the set of parameters par tends toward the measured profile $F_{x_i,y_i}$. In each iteration q, a deviation $\varepsilon^q$ between the measured profile $F_{x_i,y_i}$ and a profile $F(par^q)$ is determined. The notation $par^q$ corresponds to the set of parameters taken into account in iteration q. The deviation $\varepsilon^q$ may be a mean square deviation or a mean deviation between the measured profile $F_{x_i,y_i}$ and the profile $F(par^q)$. It is preferably a question of a scalar. The set of parameters $par^{q+1}$ of the following iteration q+1 is determined so as to minimize the deviation $\varepsilon^{q+1}$ between the measured profile $F_{x_i,y_i}$ and the profile $F(par^{q+1})$ established using the set of parameters $par^{q+1}$. Thus, each iteration q aims to estimate a set of parameters q+1 allowing the deviation to be minimized. The method is reiterated until stoppage of the iterations, this stoppage corresponding to the obtainment of a convergence criterion or of a preset number of iterations.

The set of parameters $par^{q+1}$ considered in the following iteration may be estimated using a gradient-descent algorithm, during which, in each iteration q, a gradient of the deviation $\nabla \varepsilon^q$ is determined, the latter corresponding to a variation in the deviation $\varepsilon^q$ as a function of one or more parameters, and preferably each parameter, of the set of parameters $par^q$. The set of parameters $par^{q+1}$ taken into account in the following iteration is determined depending on $\nabla \varepsilon^q$, so as to minimize the deviation $\varepsilon^{q+1}$.

Substeps 133a, 133b and 133c of substep 133, respectively corresponding to the formation of the modelled profile $F(par^q)$ and to the computation of the deviation $\varepsilon^q$ and its gradient $\nabla \varepsilon^q$, so as to define the parameters $par^{q+1}$ to be taken into account in the following iteration, have been shown in FIG. 2B.

In the first iteration (q=1), the iterative algorithm is initialized with an initial set of parameters $par^{q=1}$. The initial set of parameters may be preset.

According to another option, the two embodiments described above are combined: a database of profiles is used and the set of parameters $par_i$ that minimizes the comparison between the profiles of the database F(par) and the measured profile $F_{x_i,y_i}$ is determined. Next, the set of parameters corresponding to the observed cell is gradually adjusted using an iterative adjusting algorithm, for example, of gradient-descent type. The iterative adjusting algorithm is then initialized with the set of parameters $par_i$.

Following step 130, the refractive index $n_i$ or the relative refractive index $\Delta n_i$ is known for all or some of the cells detected in step 120. It will be noted that this is an average value established for each cell in question, i.e. with no distinction between the nucleus and the cytoplasm.

In some embodiments, the refractive index $n_m$ of the culture medium may be previously known or measured. For example, beads of known refractive index might be added to the culture medium, so as to determine indirectly the refractive index of the medium. As previously shown, with respect to cells, it is possible to estimate the relative index of those beads from the acquired image $I_0$. The refractive index of the medium may be derived therefrom.

In one possible embodiment, the fluidic chamber in which the sample lies comprise at least one pattern of known refractive index. The pattern may have been previously etched or molded in a wall of the fluidic chamber, and preferably on the bottom or on the cover of the fluidic chamber. It is then possible to estimate the relative index of the pattern from the acquired image $I_0$. The refractive index $n_m$ of the medium may be derived therefrom. The pattern may have a predefined shape, for example a spheric, hemispheric or a cubic shape.

In the next steps, the relative refractive index $\Delta n_i$ of cells will be considered. When the refractive index $n_m$ of the culture medium $10m$ is known, or considered to be known, the refractive index $n_i$ of each cell can be derived. In this case, the following steps might be carried out based on the refractive index $n_i$ of each cell.

Step 140

In this step, an index of interest $\mathcal{N}_{i\,i}$ is determined for each cell in question. According to one option, the index of interest $\mathcal{N}_{i\,i}$ may correspond to the real part of the refractive index, or of the relative refractive index. In other words, $\mathcal{N}_{i\,i}=\mathrm{Re}(n_i)$ or $\mathcal{N}_{i\,i}=\mathrm{Re}(\Delta n_i)$.

Preferably, the index of interest is established from a difference between the real part and the imaginary part of the refractive index or of the relative refractive index. Thus, $\mathcal{N}_{i\,i}=\mathrm{Re}(n_i)-\mathrm{Im}(n_i)$ or $\mathcal{N}_{i\,i}=\mathrm{Re}(\Delta n_i)-\mathrm{Im}(\Delta n_i)$.

FIG. 6A schematically shows the results of measurements observed by the inventors. The x-axis corresponds to the real part of the relative refractive index $\Delta n_i$ and the y-axis corresponds to the imaginary part of the relative refractive index $\Delta n_i$ of a cell $10_i$. Each point corresponds to a relative refractive index of a cell. The inventors have observed that the relative refractive index varies as a function of the state of the cell. In FIG. 6A, 4 types of population may be distinguished between: living cells (population c), dead cells (population d) and cellular debris (population z). The inventors have also observed the formation of a population (population p) that corresponds to cells in a transitional apoptosis state. Cells in apoptosis, in particular, at the start of apoptosis, have a relative refractive index (or refractive index) the real part of which is higher than the real part of the relative refractive index (or refractive index) of living cells. Likewise, the latter have a relative refractive index higher than dead cells. Dead cells have a relative refractive index, which real part is higher than cellular debris. Thus, the real part of the relative refractive index allows cells to be classified as a function of their state, including the apoptosis state. This shows that the index of interest $\mathcal{N}_{i\,i}$ may be established from the real part of the relative refractive index $\Delta n_i$ (or of the refractive index $n_i$).

A more precise classification may be established by combining the real part and the imaginary part of the relative refractive index (or of the refractive index), and more precisely by determining a weighted difference between the real part and the imaginary part. Thus, the index of interest may be established from the weighted difference between the real part and the imaginary part. It may be a question of a simple difference such that $\mathcal{N}_{i\,i}=\mathrm{Re}(n_i)-\mathrm{Im}(n_i)$ or $\mathcal{N}_{i\,i}=\mathrm{Re}(\Delta n_i)-\mathrm{Im}(\Delta n_i)$. Generally, it may be a question of a weighted difference such that $\mathcal{N}_{i\,i}=k_1\mathrm{Re}(n_i)-k_2\mathrm{Im}(n_i)$, or $\mathcal{N}_{i\,i}=k_1\mathrm{Re}(\Delta n_i)-k_2\mathrm{Im}(\Delta n_i)$ where $k_1$ and $k_2$ are strictly positive real numbers.

It has been observed that the real part of the refractive index is at least 5 or 10 times larger than the imaginary part. Thus, the index of interest is mainly governed by the value of the real part.

Step 150: Classification

The classification aims at determining a state of a cell $10_i$ based on the index of interest $\mathcal{N}_{i\,i}$.

According to an embodiment, a first threshold is taken into account. The index of interest of each cell $10_i$ is compared with the first threshold. Based on the comparison, the cell $10_i$ is considered either in apoptosis or not in apoptosis. A second threshold may also taken into account. The index of interest of each cell $10_i$ is compared with the second threshold. Based on the comparison, the cell is considered as living or dead. Basically, the index of interest of living cells lie between the first threshold and the second threshold. The first and second thresholds may be predefined, based on experience, of defined on a case by case basis. With reference to FIG. 6B, the first threshold is $\mathcal{N}_{i\,max}$ and the second threshold is $\mathcal{N}_{i\,min}$. $\mathcal{N}_{i\,max}$ and $\mathcal{N}_{i\,min}$ are further described below.

According to an embodiment, a distribution, corresponding to a histogram of the indices of interest determined in step 140, is established for all or some of the cells detected in step 120. Such a distribution is shown in FIG. 6B. The distribution contains a reference peak, lying around a reference value $\mathcal{N}_{i\,ref}$. The reference peak corresponds to values of the index of interest corresponding to living cells. The reference value $\mathcal{N}_{i\,ref}$ may be a mean value or a median value of the reference peak. The distribution may contain an auxiliary peak, lying around an auxiliary value $\mathcal{N}_{i\,aux}$. The auxiliary peak corresponds to dead cells. The auxiliary value $\mathcal{N}_{i\,aux}$ may be a mean value or a median value of the auxiliary peak. When most of the cells are living, the reference peak is larger than the auxiliary peak. When most of the cells are dead, the auxiliary peak is larger than the reference peak. The reference value $\mathcal{N}_{i\,ref}$ may lie within a predefined range. The same goes for the auxiliary value $\mathcal{N}_{i\,aux}$. In a specific case, it is assumed that most of the cells are living. In this case, the larger peak corresponds to the reference peak, i-e living cells.

The distribution may contain other peaks, corresponding to values of the index of interest representative of the debris and apoptosis states, respectively.

The distribution may be fitted by constrained fitting, so as to fit each peak with a predetermined parametric statistical distribution, a Gaussian distribution, for example. The fit may furthermore make provision for a number of peaks equal to 2 (living cells-dead cells), 3 (dead cells-living cells-apoptosis) or 4, (debris-dead cells-living cells-apoptosis) and/or or a specified range of the FWHM (Full Width at Half Maximum) of each peak.

When the index of interest $\mathcal{N}_i$ of a cell is contained in the reference peak, i.e. it is contained in a reference range $\Delta_{ref}$ defined about the reference value $\mathcal{N}_{ref}$, the cell is considered to be living. This corresponds to the peak identified "a" in FIG. 6B. The reference range $\Delta_{ref}$ delineating the peak is comprised between a minimum limit $\mathcal{N}_{min}$ and a maximum limit $\mathcal{N}_{max}$, $\mathcal{N}_{min}<\mathcal{N}_{max}$. The reference range $\Delta_{ref}$ may be defined manually, or on the basis of an indicator, the standard deviation, for example, of the dispersion of the reference peak.

In the example shown on FIG. 6B, when the index of interest $\mathcal{N}_i$ is lower than the minimum limit $\mathcal{N}_{min}$, the cell is classified as dead, the lowest values of the index of interest corresponding to cellular debris. In FIG. 6B, the peaks identified "z" and "d" correspond to debris and dead cells respectively.

The inventors have observed that when the index of interest $\mathcal{N}_i$ is higher than the maximum limit $\mathcal{N}_{max}$, the cell in question may be considered to be following an apoptotic process. This corresponds to the peak identified "p" in FIG. 6B.

Thus, on the basis of the real part of the refractive index of a cell, or of the relative refractive index, and preferably on the basis of the real part and of the imaginary part of these indices, the invention allows cells to be classified into at least three states: dead cell, living cell and apoptosis.

The detection of the occurrence of apoptosis may allow the user of the bioreactor to be warned of a potential degradation in the culture conditions. This allows remedial actions to be taken so as to re-establish more favourable cultural conditions, the objective being to increase cellular viability. It may be a question of modifying physicochemical conditions of the bioreactor, for example, adding nutrients or peptides, or anti-apoptotic products or modifying the stirring.

The classification may be carried out by establishing an index of interest, as described above. Other classification algorithms may be implemented, on the basis of the real part and of the imaginary part of the refractive index or of the relative refractive index. The classification algorithms may be supervised algorithms based on PCA (principal component analysis), an SVM (support vector machine), or a neural network.

The results of the classification may allow a viability of the sample to be established. The viability corresponds to a proportion of living cells relative to a number of cells identified in the acquired image or in the observation image.

Step 160: Reiteration

Steps 100 to 150 may be reiterated at various measurement times, allowing the state of the cells to be tracked as a function of time. The analyzed sample, at each measurement time, may have been sampled from a bioreactor. Alternatively, the device described with reference to FIG. 1 may take the form of a probe plunged into the bioreactor and allow the state of the cells to be tracked in situ.

By implementing the invention at various measurement times, in a given cell culture medium, the inventors have observed that the values of the refractive index or of the relative refractive index may vary over time, without the variation being explained by a change regarding the state of the cells. This is the result of a gradual variation, over time, in the refractive index of the culture medium. This may, for example, be due to the absorption of nutrients, such as sugar, by the cells. As the culture medium becomes poorer in nutrients, its index may decrease relative to that of the cells. As a result, the relative refractive index increases whatever the state of the cells. This results in a gradual shift in the relative refractive index $\Delta n_i$, and notably in the real part of the relative refractive index, as shown in FIG. 6C, which illustrates a shift of FIG. 6A, and FIG. 6D, which illustrates a shift in FIG. 6B.

It is possible to estimate this shift. The simplest way is to estimate the shift affecting the real part of the relative refractive index of the living cells. This shift may be obtained by computing a statistical value, such as the mean or median, of the relative refractive index of the living cells. When an index of interest such as described with reference to FIG. 6B is used, the shift may be determined by estimating the shift $\delta \mathcal{N}_{ref}$ a function of time in the reference peak (corresponding to the population of living cells) between two successive measurement times. Generally, the variation in the refractive index of the culture medium may be determined by estimating a variation in the relative refractive index of cells belonging to a predetermined class (dead, living, apoptosis). It is preferable to choose the class having the highest population, for example, living cells.

Under other culture conditions, the refractive index of the culture medium may gradually increase, this leading to a gradual decrease in the relative refractive index of the cells. Just as explained in the preceding paragraph, the variation in the index of the culture medium may be estimated by analyzing the variation in the real part of the relative refractive index of one cell category, living cells, for example.

Reiterating steps 100 to 150 regularly allows the gradual variation in the reference range $\Delta_{ref}$, the latter corresponding to the index of interest of the living cells, to be tracked. In the first iteration, or the first iterations of steps 100 to 150, the reference range is easily delineated, considering that most cells are living.

The inventors have implemented the method such as described with reference to steps 100 to 150 on CHO cells. The light source was a light-emitting diode emitting at 450 nm, the spectral width being 15 nm. The culture medium was a protein and serum-free, chemically-defined medium for CHO cell cultures. The image sensor was a CMOS IDS 1492 LE sensor. The concentration of cells ranged from 0 to 50 million per mL. The volume of each sample was 3 µL. The distance between the sample and the image sensor ranged between 1200 µm and 1300 µm. The distance between the sample and the light source was 5 cm. Measurements were carried out on samples of cellular suspensions originating from bioreactors. Less than one hour was required to characterize the 48 samples. The duration of each measurement is estimated to be about 30 seconds.

FIG. 7A shows a distribution of an obtained index of interest, such that $\mathcal{N}_{i\ i}=1000\text{Re}(n_i)-1000\text{Im}(n_i)$, in a first bioreactor, as a function of time. The x-axis corresponds to days, whereas the y-axis corresponds to the value of the index of interest: the signs + and − indicate the direction of variation in the index of interest: it becomes greater as it gets closer to the + sign. The greyscale represents an amount of cells for each value of index of interest. The darker the greyscale, the higher the amount of cells.

During the first days of culture, the distribution of the indices of interest contains only a single peak, which corresponds to living cells. The peak is observed to shift as the days pass. A segmentation of the distribution into a plurality of peaks, notably over the course of days 9 to 13. A substantial amount of apoptosis seems to occur on days 9 to 12 (encircled regions "p"), which is accompanied by an increase in dead cells (encircled regions "d") starting from day 12. The living cells correspond to the regions "a".

FIG. 7B shows, in the first bioreactor, a variation over the course of a number of days, in a viability (proportion of living cells relative to all of the cells counted in the sample, in %—curve 1), and the viable cells concentration (VCC) in the medium (millions of viable cells/mL—curve 2). The FIG. 7B shows a decrease in the viability starting from day 11. Both VCC and viability were established with a reference method (cellular viability system Vi-Cell—manufacturer: Beckman Coulter).

FIG. 7C shows a viability (curve 1) as well as a number of cells having a high index of index interest (curve 2), as a function of time (days), in a second bioreactor. In FIG. 7C, the viability was established using a reference method. The reference method employed marking with trypan blue and used the cellular viability system Vi-Cell. A noteworthy result is that the increase in the number of cells with a high refractive index, observed from day 10, occurs prior to the decrease in the viability established using the reference method. The drop in viability is only observable from day 12.

Thus, the invention allows a decrease in cellular viability to be anticipated by taking into account high indices of interest, i.e. by detecting and counting cells with the index of interest which is located above the reference range $\Delta_{ref}$, corresponding to living cells. This makes it possible to:
- define a reference range $\Delta_{ref}$, corresponding to indices of interest of cells considered to be living;
- count the number of cells the index of interest of which is higher than the reference range $\Delta_{ref}$. When this number exceeds a certain rate, the viability of the sample is considered to be liable to decrease. A warning may then be sent, so that adequate arrangements are made with respect to the cellular culture conditions.

The inventors have compared results, relative to the cellular viability of CHO cells, with reference measurements obtained using flow cytometry and a fluorescent marker. The percentage of cells deemed by the two methods (invention and reference measurements) were compared. The measurements were carried out in a third bioreactor:
- living and healthy, this corresponding to indices of interest located in the reference range $\Delta_{ref}$ when the invention is implemented (see FIG. 8 a-left: invention—a-right: flow cytometer);
- dead, this corresponding to indices of interest located below the reference range $\Delta_{ref}$ when the invention is implemented (see FIG. 8 d-left: invention—d-right: flow cytometer);
- in apoptosis, and more precisely at the start of apoptosis, this corresponding to indices of interest located above the reference range $\Delta_{ref}$ when the invention is implemented (see FIG. 8 p-left: invention—p-right: flow cytometer).

These percentages were calculated on days 1, 3, 6, 8 and 10.

FIG. 8 shows, for each day:
- cells considered to be living and healthy: columns a-left implementing the invention and a-right implementing the reference method;
- cells considered to be dead: columns d-right implementing the invention and d-left implementing the reference method;
- cells considered to be in early apoptosis: column p-right implementing the invention and p-ref implementing the reference method.

FIG. 8 shows that a correlation may be established between the results of the implementation of the invention and of the reference method. These results tend to confirm that cells having a high index of interest, i.e. one above the reference range $\Delta_{ref}$, are cells in the apoptosis state, and more particularly in the state of early apoptosis.

The inventors have tracked as a function of time the index of interest of CHO cells using a device such as described above. FIGS. 9A and 9B show the variation in the index of interest (y-axis) as a function of time (x-axis—hours) respectively when two cells undergo necrosis. FIGS. 9C and 9D show the variation in the index of interest (y-axis) as a function of time (x-axis—hours) respectively when two cells undergo an apoptotic phase preceding cell death. FIGS. 9A and 9B initially show that the index of interest is located in the reference range $\Delta_{ref}$ bearing witness to the fact that the cell is living. Next, the index of interest drops below the reference range $\Delta_{ref}$ this being a signature of cell death. FIGS. 9C and 9D initially show that the index of interest is located in the reference range $\Delta_{ref}$ bearing witness to the fact that the cell is living. Next, these figures show a temporary increase in the index of interest, to above the reference range $\Delta_{ref}$ during the apoptosis phase. The temporary increase in the index of interest is followed by a decrease in the index of interest below the reference range $\Delta_{ref}$ this corresponding to the death of the cell. In FIGS. 9A to 9D, the index of interest is such that: $\mathcal{N}_{i,i}=1000\text{Re}(n_i)-1000\text{Im}(n_i)$.

FIGS. 9A to 9D that considering a threshold of 40 makes it possible to classify living cells and apoptosis. Considering a threshold of 20 makes it possible to classify living cells and dead cells. According to the experience reported on FIGS. 9A to 9D, the reference range $\Delta_{ref}$ might extend between $\mathcal{N}_{i\,min}=20$ and $\mathcal{N}_{i\,max}=40$.

In each of these figures, the phases in which the cell is living, dead and where appropriate in apoptosis have been indicated by the letters a, d and p.

Other Embodiments

In the above description, the relative refractive index was determined in step 130 using the principles described in patent application FR1859362 (or U.S. Ser. No. 16/595,661). There are other variants, allowing the refractive index or the relative refractive index to be estimated.

According to a first variant, the relative refractive index may also be estimated as described in patent application FR1859618 (or in the U.S. patent application Ser. No. 16/655,300), and more particularly in steps 110 to 160 of the latter.

Such an approach is described in FIG. 10A. Step 130 is replaced with step 230. Step 230 comprises substeps.

In a substep 231, the sample is described by a distribution of the sets parameters at various radial positions within the sample plane. Each radial position corresponds to a position within the sample plane. Each position of the sample plane is associated with a set of parameters. Each set of parameters comprises a term representative of an optical parameter of the sample. At least one optical parameter is an optical path difference induced by the sample, at the radial position.

The method comprises, following the acquisition of an image of the sample:
- a) substep 232: taking into account a complex image of the sample, depending on the parameters of the sample, the complex image of the sample preferably being defined in a plane parallel to the detection plane;
- b) substep 233: propagating the complex image of the sample, i.e. the image defined in step a), to the detection plane; the propagation implements a propagation operator such as described above with reference to step 120;
- c) substep 234: comparing the image resulting from b) with the image $I_0$ of the sample acquired by the image sensor 16;
- d) substep 235: depending on the comparison, updating parameters describing the sample;
- e) sub-step 236: reiterating steps a) to e) while updating, in each iteration, the complex image of the sample using the parameters updated in step d) of a proceeding iteration.

With this approach:
in the first iteration, the complex image of the sample is preferably established using initial parameters.

step d) may comprise determining a validity indicator, such that the parameters of the sample are updated so as to minimize the validity indicator. This minimization may be achieved using a gradient-descent algorithm, a gradient of the validity indicator being computed as a function of one or more parameters of the sample, which parameters are defined in each radial position. This step of computing the validity indicator and of updating the parameters of the sample is described with respect to steps 140 and 150 in patent application FR1859618 (or in the U.S. patent application Ser. No. 16/655,300).

the parameters of the sample may be defined as described in FR1859618 (or in the U.S. patent application Ser. No. 16/655,300). It may, in particular, be a question of an absorbance $\alpha(r)$ and of a difference in optical path length $L(r)$. r is the radial position within the sample plane $P_{10}$. When the sample plane is parallel to the detection plane, $r=(x, y)$, where $(x, y)$ are coordinates within the detection plane $P_0$.

FIG. 10B shows a detail of a cell 10*i* of the sample. In FIG. 10B, the wave front of the light wave 12 incident on the sample, and of the exposure light wave 14 have been represented by dashed lines. In this example, $n_i > n_m$. The wave front is plane before reaching the sample. Downstream of the sample, the wave front is deformed because of the appearance of optical path differences induced by the cell.

Taking into account a thickness $e(r)$ of the cell at a radial position r, the refractive index may be estimated from the difference in optical path length $L(r)$. The thickness of the cell $e(r)$ is, for example, determined by estimating a radius or a diameter of each cell, from the observation image. From the thickness, it is possible to determine the volume V of the cell under the assumption of a shape, typically a circle shape.

Knowing the difference in optical path length $L(r)$, as well as the volume V of a cell, the real and imaginary parts of the relative refractive index may be determined using the following expressions:

$$\text{Re}(\Delta n_i) = \frac{1}{V} \int_V L(r) dr \quad (1)$$

$$\text{Im}(\Delta n_i) = -\frac{\lambda}{2\pi V} \int_V \alpha(r) dr \quad (2)$$

According to this variant, the observation image I' of the sample may be obtained from a spatial reference distribution of one of the parameters in question (the absorbance and/or the difference in optical path length). Thus, according to this variant, step 120 described above is not necessary.

According to a second variant, the absorbance $\alpha(r)$ and difference $L(r)$ in optical path length may be estimated as described in patent application FR1906766, and more particularly with respect to steps 110 to 180 of FR1906766. Patent application FR1906766 may be considered to be an improvement of patent application FR1859618. The real and imaginary parts of the relative refractive index are estimated using expressions (1) and (2).

According to a third variant, the real and imaginary parts of the relative refractive index are obtained by carrying out, on the acquired image $I_0$, the operations described in patent application FR1873260, and more precisely with respect to steps 100 to 150 in FR1873260. With such an approach, step 130 of the present patent application is replaced with step 330: see FIG. 11. Step 330 comprises the following substeps:

i. substep 331: reconstructing a complex image in the sample plane, using the principles described with reference to step 120 of the present patent application;

ii. substep 332: selecting a region of interest of the complex image, corresponding to a cell and preferably to a single cell;

iii. substep 333: forming a complex image, called the extracted complex image, from the region of interest selected in ii);

iv. substep 334: applying a propagation operator to the extracted complex image resulting from iii), in order to obtain, in a propagation plane, a diffraction pattern corresponding to the cell corresponding to the region of interest selected in ii);

v. substep 335: characterizing the cell from the diffraction pattern obtained in iv).

The characterization of the diffraction pattern may comprise a comparison with a modelled diffraction pattern. The modelled diffraction pattern may have been modelled using a Mie model, taking into account a complex refractive index or a complex relative refractive index.

This approach amounts to modelling not a profile of a quantity relative to complex amplitude, along the transverse axis, as described with reference to step 130, but a diffraction pattern formed by the cell. It is a question of determining the parameters of the cell, notably the complex refractive index, or the relative complex relative index, allowing a modelled diffraction pattern considered to be similar to the diffraction pattern obtained in substep iv) to be obtained. Substeps ii) to iv) aim to consider in isolation one single cell, so as to obtain, in the propagation plane, a single diffraction pattern corresponding to said cell. The propagation plane is preferably the detection plane.

FIG. 12 schematically shows a device allowing the invention to be implemented. Contrary to the device shown in FIG. 1, the device of FIG. 12 comprises an optical image-forming system 19. The optical system 19 defines an image plane and an object plane. The optical system may be a lens or an objective. During the acquisition of the image of the sample, the image sensor is placed in a defocused configuration. The detection plane is offset with respect to the image plane and/or the plane in which the sample lies is offset with respect to the object plane. The offset is generally small, preferably being smaller than 1 mm, and typically lying in a range 50 μm-500 μm.

The invention will possibly be used to characterize the variation in the viability state of cells cultivated in bioreactors, for example, in the field of the pharmaceutical industry. It allows the viability state of cells to be tracked and a decrease in the viability of the cells to be prevented. One advantage is that it allows the decrease in cell viability to be anticipated, this allowing suitable measures to be taken, with respect to the culture conditions, to prevent too great a degradation in cellular viability.

The invention claimed is:

1. A method for determining a state of a cell, the cell being placed in a sample in contact with a culture medium, the method comprising:
    a) illuminating the sample with a light source and acquiring an image of the sample with an image sensor, the image sensor lying in a detection plane;
    b) from the acquired image, locating a position of the cell in a plane parallel to the detection plane;
    c) from the acquired image, estimating a refractive index of the cell or a relative refractive index of the cell, the relative refractive index corresponding to the refractive index of the cell relative to the refractive index of the culture medium;
d) from the estimation of the refractive index or of the relative refractive index, determining an index of interest of the cell; and
e) from the index of interest, classifying a state of the cell among predetermined states, the predetermined states comprising at least one apoptosis state and one living state, wherein:
in c), the refractive index or the relative refractive index is a complex quantity;
in d), the index of interest is determined depending, on at least one of:
  a real part of the refractive index or of the relative refractive index; and
  an imaginary part of the refractive index or of the relative refractive index.

2. The method according to claim 1, wherein the index of interest is determined from a difference or from a weighted difference between the real part and the imaginary part of the refractive index or of the relative refractive index.

3. The method according to claim 1, wherein e) comprises:
taking into account a threshold; and
comparing the index of interest with the threshold.

4. The method according to claim 1, wherein
e) comprises taking into account a reference range, the reference range comprising indices of interest corresponding to living cells; and
the apoptosis state corresponds to an index of interest outside of the reference range.

5. The method according to claim 4, wherein:
the predetermined states comprises at least one dead state; and
the dead state and the apoptosis state correspond to indices of interest lying respectively on one side and on another side of the reference range.

6. The method according to claim 4, wherein:
b) to e) are carried out for a plurality of cells, each cell of the plurality of cells being considered as living cells, so as to obtain a distribution of the index of interest of said cells; and
in e), the reference range is defined from said distribution.

7. The method according to claim 6, wherein e) comprises:
taking into account a threshold; and
comparing the index of interest with the threshold;
wherein in e), the threshold is defined from said distribution.

8. The method according to claim 6, wherein:
e) comprises determining a reference value from said distribution of the index; and
the state of each cell is determined depending on a deviation between the reference value and the index of interest of each cell.

9. The method according to claim 1, wherein:
a) is carried out at various times, so as to obtain an image of the sample at each time;
steps b) to e) are carried out successively using the images obtained at each time;
in each step e), the predetermined states comprise at least one dead cellular state; and
the method comprises a step f) of computing a viability at each time, the viability depending on a number of cells considered to be living, dead and in apoptosis, respectively.

10. The method according to claim 1, wherein:
a) is carried out at various times, so as to obtain an image of the sample each time;
steps b) to e) are carried out successively using the images obtained at each time; and
the method further comprises emitting a warning when a number of cells considered to be in the apoptosis state exceeds a predetermined value.

11. The method according to claim 1, wherein:
in a), an exposure light wave propagates towards the image sensor along a propagation axis;
step c) comprises:
  c-i) on the basis of the acquired image, applying a propagation operator, for a plurality of reconstruction distances from the detection plane so as to estimate, at each reconstruction distance, a complex amplitude of the exposure light wave;
  c-ii) on a basis of the complex amplitude estimated, at various reconstruction distances, obtaining a profile representing a variation of the complex amplitude of the exposure light wave along an axis parallel to the propagation axis and passing through the position of the cell;
  c-iii) associating each cell with a set of parameters, at least one parameter of the set of parameters depending on the refractive index of the cell or on the relative refractive index of the cell;
  c-iv) modelling a cell, taking into account a value of each parameter of the set of parameters, and modelling an exposure light wave, propagating toward the image sensor under an effect of an illumination, with the light source, of the modelled cell;
  c-v) on a basis of the modelled exposure light wave, forming a modelled profile representing a variation in the complex amplitude of the modelled exposure light wave, along an axis parallel to the propagation axis;
  c-vi) comparing the profile obtained in c-ii) with the modelled profile resulting from c-v), so as to determine the value of said at least one parameter of the cell; and
  c-vii) deriving the refractive index of the cell or the relative refractive index of the cell from the parameters associated to the cell.

12. The method according to claim 11, wherein:
c-iv) comprises modelling cells respectively having various values of refractive index, or various values of relative refractive index so as to obtain, following c-v), a database of modelled profiles, each modelled profile being associated with one refractive index, or one relative refractive index; and
c-vi) comprises minimizing a deviation between the profile resulting from c-ii) and the modelled profiles of the database, the respective values of the parameters of the cell being those minimizing the deviation.

13. The method according to claim 11, wherein steps c-iii) to c-vi) are implemented iteratively such that, in each iteration, the profile modelled in c-v) gets gradually closer to the profile obtained in c-ii).

14. The method according to claim 13, wherein each iteration comprises:

determining a deviation between the profile modelled in c-iv) of the same iteration, and the profile obtained in c-ii); and determining a gradient of the deviation as a function of at least one parameter of the set of parameters, so as to determine the values of the parameters of the cell modelled in c-iv) of a following iteration.

15. The method according to claim 1, wherein:

in step a), an exposure light wave propagates towards the image sensor;

the sample lies in a sample plane;

the sample is described by sets of parameters, each set of parameters being respectively defined at a plurality of radial positions in the sample plane, and each set of parameters comprising at least an optical parameter of the sample, at least one optical parameter being an optical path difference induced by the sample at each radial position;

step c) comprises:
- c-i) taking into account sets of parameters describing the sample, in the sample plane;
- c-ii) on a basis of the sets of parameters, forming a complex image of the sample in the sample plane;
- c-iii) applying a propagation operator to the complex image formed in c-ii), in order to compute an image of the sample in the detection plane;
- c-iv) comparing the image acquired in a) and the image computed in c-iii), in order to compute a validity indicator;
- c-v) updating the sets of parameters, so as to make the validity indicator tend toward a preset value;
- c-vi) reiterating c-ii) to c-v) taking into account the sets of parameters updated in c-v), until the validity indicator is considered as reaching the preset value;
- c-vii) estimating a radial position of a cell; and
- c-viii) estimating the refractive index or the relative refractive index of the cell from the sets of parameters defined at said at least one radial position of the cell.

16. The method according to claim 15, wherein c-v) comprises determining a gradient of the validity indicator as a function of at least one parameter, such that the sets of parameters are updated in order to decrease the validity indicator of a following iteration.

17. The method according to claim 16, wherein c-v) comprises implementing an algorithm of gradient-descent type.

18. The method according to claim 17, wherein each set of parameters comprises:
- at least one optical parameter representative of an optical path difference along a propagation axis of the exposure light; and
- an optical parameter representative of absorbance.

19. A device, comprising
a light source, configured to emit a light wave;
an image sensor, configured to acquire an image of a sample when said sample is illuminated by the light wave;
a processor, configured to process each image acquired by the image sensor, the image sensor being configured to operate steps c) to e) of the method of claim 1.

* * * * *